(12) United States Patent
Waki

(10) Patent No.: US 8,734,353 B2
(45) Date of Patent: May 27, 2014

(54) ULTRASONIC DIAGNOSTIC APPARATUS AND ELASTIC IMAGE DISPLAY METHOD

(75) Inventor: Koji Waki, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 18 days.

(21) Appl. No.: 13/201,760

(22) PCT Filed: Feb. 16, 2010

(86) PCT No.: PCT/JP2010/052263
§ 371 (c)(1),
(2), (4) Date: Aug. 16, 2011

(87) PCT Pub. No.: WO2010/098233
PCT Pub. Date: Sep. 2, 2010

(65) Prior Publication Data
US 2011/0301465 A1    Dec. 8, 2011

(30) Foreign Application Priority Data

Feb. 24, 2009  (JP) ................................. 2009-040502

(51) Int. Cl.
*A61B 8/00*  (2006.01)
(52) U.S. Cl.
USPC ......................................... 600/449; 600/437
(58) Field of Classification Search
USPC ................................................ 600/437–469
See application file for complete search history.

(56) References Cited

U.S. PATENT DOCUMENTS

| | | | |
|---|---|---|---|
| 6,270,459 B1 * | 8/2001 | Konofagou et al. ........... | 600/449 |
| 8,043,216 B2 * | 10/2011 | Matsumura ................... | 600/438 |
| 8,167,804 B2 * | 5/2012 | Kim et al. ..................... | 600/438 |
| 2008/0081994 A1 * | 4/2008 | Kim et al. ..................... | 600/438 |
| 2008/0269606 A1 * | 10/2008 | Matsumura ................... | 600/438 |
| 2012/0016238 A1 * | 1/2012 | Matsumura ................... | 600/438 |

FOREIGN PATENT DOCUMENTS

| | | |
|---|---|---|
| JP | 2000-060853 | 2/2000 |
| JP | 2005-66041 | 3/2005 |
| JP | 2007-222605 | 9/2007 |
| WO | 2005/120358 | 12/2005 |
| WO | 2005/122907 | 12/2005 |
| WO | 2006/073088 | 7/2006 |

* cited by examiner

*Primary Examiner* — Sanjay Cattungal
(74) *Attorney, Agent, or Firm* — Brundidge & Stanger, P.C.

(57) ABSTRACT

An elastic image suitable for diagnosis is easily acquired without depending on the examiner's pressure technique. The displacement of tissue in a tomographic portion of an object is measured on the basis of a pair of RF signal frame data items regarding the tomographic portion, which are obtained at different times by transmitting and receiving an ultrasonic wave to and from the object (b). The average displacement of each beam line (d0 to dn) of an ultrasonic wave is calculated (c), and a displacement gradient (50) in the scanning direction of an ultrasonic probe is calculated on the basis of the displacement average (d). A correction coefficient (52) with respect to the displacement of each beam line is calculated on the basis of the calculated displacement gradient (e), and the displacement distribution measured on the basis of the calculated correction coefficient is corrected (f). In this manner, even if the object is pressed by an ultrasonic probe inclined along the scanning direction, an elastic image generated by pressing the object with the ultrasonic probe not inclined along the scanning direction can be generated in a pseudo manner by correcting the displacement distribution on the basis of the correction coefficient.

6 Claims, 18 Drawing Sheets

ULTRASONIC DIAGNOSTIC APPARATUS AND ELASTIC IMAGE DISPLAY METHOD

TECHNICAL FIELD

The present invention relates to an ultrasonic diagnostic apparatus and an elastic image display method and in particular, to an ultrasonic diagnostic apparatus and an elastic image display method for displaying an elastic image showing the hardness or softness of tissue in a tomographic portion of an object.

BACKGROUND ART

The ultrasonic diagnostic apparatus transmits an ultrasonic wave from an ultrasonic probe into the object, receives a reflected echo signal of the ultrasonic wave corresponding to the structure of body tissue from the inside of the object, forms a tomographic image, for example, an ultrasonic tomographic image or the like, and displays it for diagnosis.

In recent years, it has been disclosed that an ultrasonic reception signal can be measured by pressing the object with an ultrasonic probe using a manual or mechanical method, displacement of each portion of the body occurring due to the pressure is calculated on the basis of frame data of two ultrasonic reception signals measured at different times, and an elastic image showing the hardness or softness of tissue in a tomographic portion of the object is generated on the basis of the displacement data (for example, Patent Document 1).

However, although the method in which an examiner operates an ultrasonic probe manually to press the object is advantageous in terms of being real time, simplicity, resolution, and cost, there is a problem that an elastic image suitable for diagnosis is not acquired if the pressure is not properly performed and this depends on the examiner's pressure technique. For example, if the object is pressed by an ultrasonic probe inclined from the surface of the object along the scanning direction, tissue of the object is not uniformly pressed. Accordingly, an elastic image may not be suitable for diagnosis.

In view of this point, for example, Patent Document 2 discloses a method of detecting the stress from a pressure sensor provided in an ultrasonic diagnostic apparatus or the stress from a material with known hardness and displaying the distribution of the stress in a scanning direction of the ultrasonic probe. In addition, for example, Patent Document 3 discloses a method of calculating the displacement distribution or the stress distribution of tissue of the object, detecting the direction of pressure applied by an ultrasonic probe on the basis of the distribution, and displaying the angle.

PRIOR ART DOCUMENT

Patent Document

[Patent Document 1] JP-A-2000-060853
[Patent Document 2] International Publication No. WO2005/120358
[Patent Document 3] International Publication No. WO2005/122907

SUMMARY OF INVENTION

Technical Problem

However, the above-described patent Citations have room for improvement in regard to acquiring an elastic image suitable for diagnosis easily without depending on the examiner's pressure technique.

That is, in each of the above-described patent Citations, a pressure state is shown to the examiner by displaying the distribution of the stress in the scanning direction of the ultrasonic probe or the direction of the pressure applied by the ultrasonic probe, in order to prompt the examiner to perform the proper pressure technique. Accordingly, since the examiner needs to operate the ultrasonic probe while viewing the display of the pressure state in order to realize an appropriate pressure state, handling may become complicated.

Therefore, it is an object of the invention to acquire an elastic image suitable for diagnosis easily without depending on the examiner's pressure technique.

Solution to Problem

An ultrasonic diagnostic apparatus of the invention is configured to include: an ultrasonic probe which transmits and receives an ultrasonic wave to and from an object; phasing addition unit configured to generate RF signal frame data of a tomographic portion of an object on the basis of a reflected echo signal measured by the ultrasonic probe; displacement measuring unit configured to measure displacement of tissue in the tomographic portion on the basis of a pair of RF signal frame data items acquired at different times; elastic information calculation unit configured to calculate elastic information indicating the hardness or softness of the tissue in the tomographic portion on the basis of the measured displacement; elastic image forming unit configured to generate an elastic image on the basis of the elastic information; and an image display unit configured to display the elastic image.

In addition, the ultrasonic diagnostic apparatus includes gradient detecting unit configured to calculate a displacement gradient in a scanning direction perpendicular to an ultrasonic wave transmission and reception direction and calculating a correction coefficient on the basis of the calculated displacement gradient, and the elastic image forming unit corrects the elastic image on the basis of the calculated correction coefficient.

In addition, gradient detecting unit configured to calculate a displacement gradient in the scanning direction of the ultrasonic probe on the basis of displacement of each beam line of an ultrasonic wave of tissue in a tomographic portion and calculate a correction coefficient with respect to the displacement of each beam line on the basis of the calculated displacement gradient is included, and an elastic image is generated by correcting the displacement measured on the basis of the calculated correction coefficient.

That is, when the object is pressed by the ultrasonic probe inclined along the scanning direction, a gradient occurs in the displacement of the scanning direction of tissue in a tomographic portion of the object. By calculating a correction coefficient for correcting the inclination of the ultrasonic probe on the basis of the displacement gradient in the scanning direction and correcting the measured displacement on the basis of the correction coefficient, an elastic image generated when the object is pressed by the ultrasonic probe not inclined along the scanning direction can be generated in a pseudo manner. As a result, the examiner can acquire an elastic image suitable for diagnosis easily without depending on the examiner's pressure technique.

In this case, the gradient detecting unit may correct a displacement gradient in the scanning direction on the basis of an average displacement of each beam line and calculate a correction coefficient for displacement of each beam line on the basis of the corrected displacement gradient.

In addition, the gradient detecting unit may correct a displacement gradient in the scanning direction on the basis of a stress distribution coefficient in the scanning direction of the ultrasonic probe set in advance and calculate a correction coefficient for displacement of each beam line on the basis of the corrected displacement gradient. That is, at both ends of the ultrasonic probe in the scanning direction, stress at the time when the object is pressed tends to be distributed outside from both the pressed ends of the object. Accordingly, the stress distribution tends to be convex along the scanning direction. Therefore, by setting a stress distribution coefficient in the scanning direction of the ultrasonic probe in advance, correcting the displacement gradient in the scanning direction on the basis of the stress distribution coefficient, and calculating a correction coefficient on the basis of the corrected displacement gradient, the accuracy of the correction coefficient can be improved.

In addition, the gradient detecting unit may calculate a displacement gradient feature value on the basis of the displacement gradient in the scanning direction for each frame of displacement of tissue in a tomographic portion based on a pair of RF signal frame data items acquired at different times, and image mixing unit configured to generate the elastic image by selecting a plurality of displacement frames each of which has a smaller displacement gradient feature value than a threshold value set in advance, a plurality of elastic information frames based on the plurality of displacement frames, or a plurality of elastic image frames based on the plurality of displacement frames and mixing the plurality of selected frames may be included.

That is, generation of an elastic image with a high S/N ratio obtained by removing noise components by performing smoothing processing, which is represented by persistence processing, between frames acquired at different times is known. According to the invention, since only frames with smaller displacement gradient feature values than the threshold value set in advance, that is, only frames obtained by pressing the object in a state where the inclination of the ultrasonic probe along the scanning direction is allowable are selected and mixed, it is possible to obtain an elastic image with higher accuracy.

In addition, the image mixing unit may select a plurality of displacement frames each of which has a smaller displacement gradient feature value than the threshold value set in advance, corrects each of the plurality of selected displacement frames on the basis of a correction coefficient with respect to the displacement of each beam line, selects the plurality of corrected displacement frames, a plurality of elastic information frames based on the plurality of corrected displacement frames, or a plurality of elastic image frames based on the plurality of corrected displacement frames, and mixes the plurality of selected frames to generate an elastic image. According to this, since only frames obtained by pressing the object in a state where the inclination of an ultrasonic probe along the scanning direction is allowable are selected and these frames are corrected on the basis of a correction coefficient in a pseudo manner in a state where there is no inclination and are then mixed, the accuracy of an elastic image can be further improved.

In addition, when generating an elastic image by pressing tissue in a tomographic portion of the object using pulsation caused by the blood flow, the gradient detecting unit may be configured to calculate a tilt angle of the scanning direction of the ultrasonic probe with respect to the pressure direction by pulsation on the basis of the displacement gradient in the scanning direction and change the beam angle of an ultrasonic wave according to the calculated tilt angle.

That is, when pressing the tissue in a tomographic portion of the object using pulsation, it is preferable to dispose an ultrasonic probe so that vectors of the pressure direction by pulsation and the transmission and reception direction of an ultrasonic beam are the same or opposite. In other words, it is preferable that the pressure direction by pulsation and the ultrasonic wave transmission and reception surface of the ultrasonic probe be perpendicular to each other. However, it may be difficult to dispose the ultrasonic probe in such a preferable state. Therefore, it is calculated how much the scanning direction (ultrasonic wave transmission and reception surface) of the ultrasonic probe is inclined from the pressure direction by pulsation on the basis of the displacement gradient in the scanning direction, and the beam angle of an ultrasonic wave is changed so that vectors of the beam transmission and reception direction of an ultrasonic wave and the pressure direction by pulsation are the same or opposite. As a result, it is possible to make an elastic image using pulsation more suitable for diagnosis.

In addition, an elastic image display method includes: a step of transmitting and receiving an ultrasonic wave; a step of measuring displacement on the basis of a measured reflected echo signal and forming an elastic image on the basis of the displacement; a step of displaying the elastic image; a step of calculating a displacement gradient in a scanning direction perpendicular to an ultrasonic wave transmission and reception direction; a step of calculating a correction coefficient on the basis of the calculated displacement gradient; and a step of correcting the elastic image on the basis of the calculated correction coefficient. The examiner can acquire an elastic image suitable for diagnosis easily without depending on the examiner's pressure technique.

Advantageous Effects of Invention

According to the invention, the examiner can acquire an elastic image suitable for diagnosis easily without depending on the examiner's pressure technique.

DESCRIPTION OF EMBODIMENTS

Figure 1:
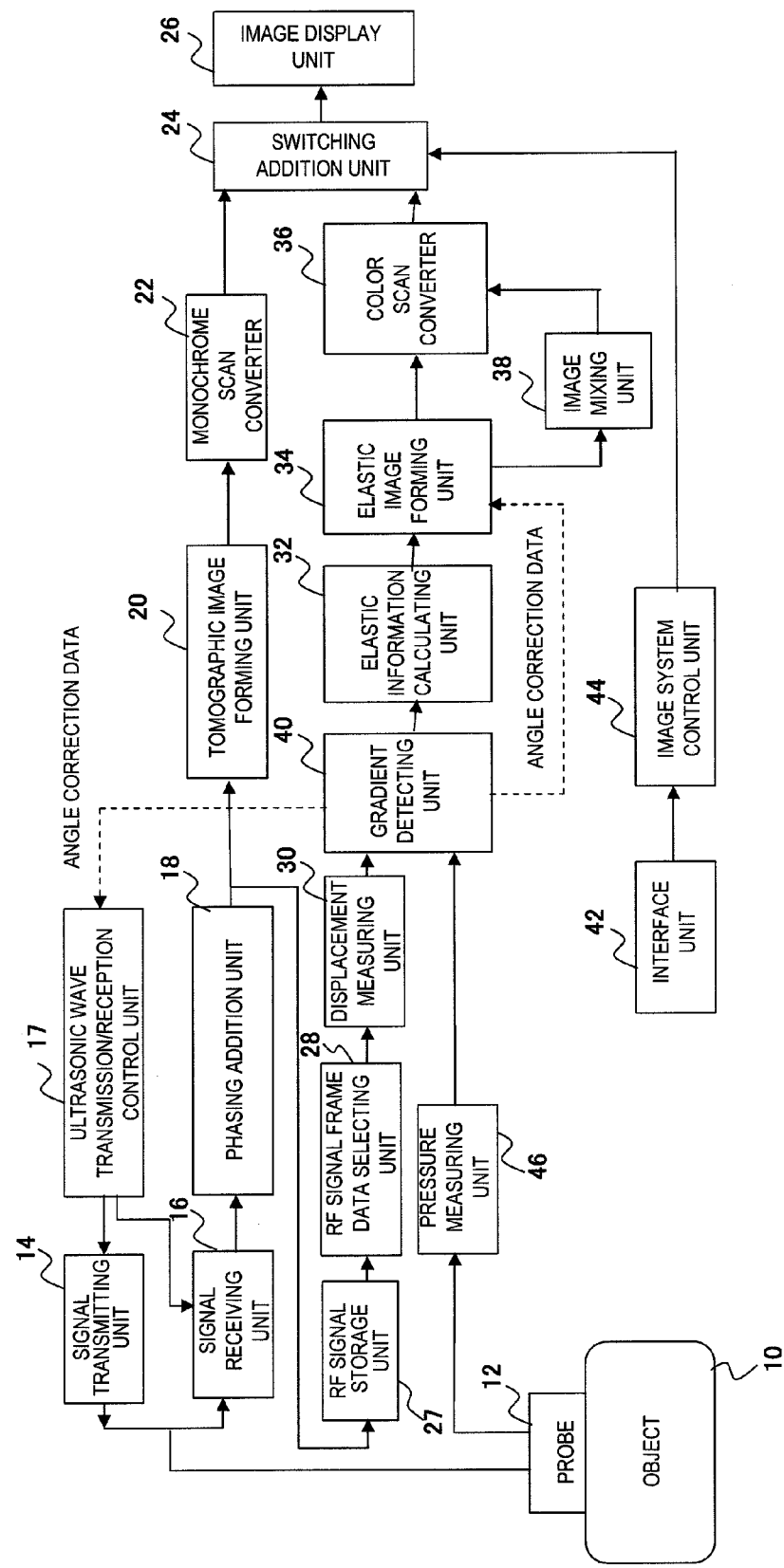
FIG. 1 is a block diagram showing the entire configuration of an ultrasonic diagnostic apparatus of the present embodiment.

Hereinafter, embodiments of an ultrasonic diagnostic apparatus to which the invention is applied will be described. Moreover, in the following explanation, the same reference numerals are given to the same functional components, and repeated explanation thereof will be omitted.

FIG. 1 is a block diagram showing the entire configuration of an ultrasonic diagnostic apparatus of the present embodiment. As shown in FIG. 1, an ultrasonic diagnostic apparatus 1 includes: an ultrasonic probe 12 used in contact with an object 10; a signal transmitting unit 14 which transmits an ultrasonic wave repeatedly to the object 10 through the ultrasonic probe 12 at intervals; a signal receiving unit 16 which receives time-series reflected echo signals generated from the object 10; an ultrasonic wave transmission/reception control unit 17 which controls the signal transmitting unit 14 and the signal receiving unit 16; and a phasing addition unit 18 which performs phasing addition of the reflected echoes received by the signal receiving unit 16.

In addition, the ultrasonic diagnostic apparatus 1 includes: a tomographic image forming unit 20 which forms a tomographic gradation image of the object, for example, a monochrome tomographic image of the object on the basis of RF signal frame data from the phasing addition unit 18; and a monochrome scan converter 22 which converts an output signal of the tomographic image forming unit 20 so as to be suitable for the display of an image display unit 26.

In addition, the ultrasonic diagnostic apparatus 1 includes: an RF signal storage unit 27 which stores the RF signal frame data output from the phasing addition unit 18; an RF signal frame data selecting unit 28 which selects at least two items of the stored RF signal frame data; a displacement measuring unit 30 which measures the displacement of body tissue of the object 10 on the basis of at least two items of the RF signal frame data acquired at different times; and a gradient detecting unit 40 which detects a displacement gradient or the like in the scanning direction of the ultrasonic probe 12 on the basis of the output from the displacement measuring unit 30. Details of the gradient detecting unit 40 will be described later.

In addition, the ultrasonic diagnostic apparatus 1 includes: an elastic information calculating unit 32 which calculates the elastic information including the distortion or the elastic modulus from the displacement information measured by the displacement measuring unit 30; an elastic image forming unit 34 which forms a color elastic image from the distortion or the elastic modulus calculated by the elastic information calculating unit 32; a color scan converter 36 which converts the output signal of the elastic image forming unit 34 so as to be suitable for the display of the image display unit 26; and an image mixing unit 38 which performs smoothing processing, such as persistence processing, between the elastic image frames acquired at different times, which are output from the elastic image forming unit 34, and outputs the result to the color scan converter 36.

In addition, the ultrasonic diagnostic apparatus 1 includes: a switching addition unit 24 which makes the monochrome tomographic image output from the monochrome scan converter 22 and the color elastic image output from the color scan converter 36 overlap each other, displays these images in parallel, or performs switching; and the image display unit 26 which displays an image output from the switching addition unit 24. In addition, the ultrasonic diagnostic apparatus 1 includes: an image system control unit 44 which controls the switching addition unit 24 and other functional blocks; an interface unit 42 which gives an instruction to the image system control unit 44, such as a keyboard, a mouse, and a touch panel; and a pressure measuring unit 46 which is provided in the ultrasonic probe 12 and which detects the stress when the object 10 is pressed and outputs it to the gradient detecting unit 40.

Here, the ultrasonic diagnostic apparatus 1 will be described in detail. The ultrasonic probe 12 is formed by disposing a plurality of vibrators, and has a function of transmitting or receiving an ultrasonic wave to or from the object 10 through the vibrators. The signal transmitting unit 14 has a function of generating a transmission wave pulse for generating an ultrasonic wave by driving the ultrasonic probe and setting the convergent point of the transmitted ultrasonic wave with a certain depth.

The signal receiving unit 16 generates an RF signal, that is, a reception wave signal by amplifying the reflected echo signal received by the ultrasonic probe 12 with a predetermined gain. The phasing addition unit 18 controls the phase of the input RF signal amplified by the signal receiving unit 16, and generates the RF signal frame data by forming an ultrasonic beam at one or a plurality of convergent points.

The tomographic image forming unit 20 acquires tomographic image data by performing signal processing, such as gain correction, log compression, detection, edge enhancement, and filtering, on the input RF signal frame data from the phasing addition unit 18. In addition, the monochrome scan converter 22 is configured to include an A/D converter, which converts the tomographic image data from the tomographic image forming unit 20 into a digital signal, a frame memory which stores the plurality of converted tomographic image data items in time series, and a controller. This monochrome scan converter 22 acquires the tomographic frame data in the object, which is stored in the frame memory, as one image and reads the acquired tomographic frame data in synchronization with a television.

The RF signal frame data selecting unit 28 selects a set of RF signal frame data, that is, at least two items of the RF signal frame data from a group of a plurality of RF signal frame data items from the phasing addition unit 18 which are stored in the RF signal storage unit 27. For example, RF signal frame data from the phasing addition unit 18 generated in time series, that is, on the basis of a frame rate is sequentially stored in the RF signal storage unit 27, and the stored RF signal frame data (N) is selected as first data and at the same time, one RF signal frame data item (X) is selected from the RF signal frame data group (N-1, N-2, N-3, ..., N-M) stored in the past in terms of time. Moreover, here, N, M, and X are index numbers given to the RF signal frame data and natural numbers.

In addition, the displacement measuring unit 30 performs one-dimensional or two-dimensional correlation processing on a set of selected data, that is, the RF signal frame data (N) and the RF signal frame data (X) to calculate a displacement or movement vector in body tissue corresponding to each point of the tomographic image, that is, one-dimensional or two-dimensional displacement distribution regarding the displacement direction and size. Here, a block matching method is used to detect a movement vector. In the block matching method, processing is performed in which an image is divided into blocks with, for example, "N×N" pixels, a block in a region of interest is observed, the most similar block to the observed block is searched for from previous frames, and a sample value is determined by predictive coding, that is, by the difference referring to this.

The elastic information calculating unit 32 calculates the distortion or the elastic modulus of body tissue corresponding to each point on the tomographic image from the measurement value output from the displacement measuring unit 30, for example, the movement vector and the pressure value, which is output from the pressure measuring unit 46, and generates an elastic image signal, that is, elastic frame data, on the basis of the distortion or the elastic modulus.

In this case, the data of the distortion is calculated by spatial differentiation of the amount of movement of body tissue, for example, by spatial differentiation of the displacement. In addition, the data of the elastic modulus is calculated by dividing the pressure change by the distortion change. For example, assuming that the displacement measured by the displacement measuring unit 30 is L(X) and the pressure measured by the pressure measuring unit 46 is P(X), distortion ΔS(X) can be calculated by spatial differentiation of L(X). Accordingly, the distortion ΔS(X) can be calculated using Expression ΔS(X)=ΔL(X)/ΔX. In addition, the Young's modulus Ym(X) of elastic modulus data is calculated by Expression of Ym=(ΔP(X))/ΔS(X). Since the elastic modulus of body tissue corresponding to each point of the tomographic image is calculated from this Young's modulus Ym, it is possible to acquire the two-dimensional elastic image data continuously. In addition, the Young's modulus is a ratio of simple tensile stress applied to the body to the tensile strain occurring in parallel to the tensile stress.

The elastic image forming unit 34 is configured to include a frame memory and an image processing unit. The elastic image forming unit 34 secures the elastic frame data, which is output in time series from the elastic information calculating unit 32, in the frame memory and performs image processing on the secured elastic frame data.

The color scan converter 36 has a function of giving color information to the elastic frame data from the elastic image forming unit 34. That is, the color scan converter 36 performs conversion into three primary colors of light, that is, red (R), green (G), and blue (B) on the basis of the elastic frame data. For example, elastic data with large distortion is converted into the red code and elastic data with small distortion is converted into the blue code.

The image mixing unit 38 generates an elastic image with a high S/N ratio obtained by removing noise components by performing smoothing processing, which is represented by averaging processing, processing of calculating the median, or persistence processing, between the elastic image frames with different acquisition times output from the elastic image forming unit 34 and outputs the elastic image to the color scan converter 36. In addition, the smoothing processing may be performed not only between the elastic image frames but also between displacement frames output from the displacement measuring unit 30 or between elastic information frames output from the elastic information calculating unit 32, for example.

The switching addition unit 24 is configured to include a frame memory, an image processing unit, and an image selecting unit. Here, the frame memory stores the tomographic image data from the monochrome scan converter 22 and the elastic image data from the color scan converter 36. In addition, the image processing unit mixes the tomographic image data and the elastic image data, which are secured in the frame memory, after changing the mixing ratio. The brightness information and the color information regarding each pixel of the composite image are obtained by adding the information on the monochrome tomographic image and the information on the color elastic image with the mixing ratio. In addition, the image selecting unit selects an image, which is to be displayed on the image display unit 26, from the tomographic image data and the elastic image data in the frame memory and the composite image data of the image processing unit.

In the case of generating and displaying an elastic image as in the ultrasonic diagnostic apparatus 1 of the present embodiment, it is necessary to press tissue in a tomographic portion of the object 10. For example, the object 10 is pressed until the initial pressure state (for example, a state in which distortion of about 5% to 20% occurs) in a state where the ultrasonic probe 12 is in contact with the body surface, and the ultrasonic probe 12 is pushed or pulled from the initial pressure state so that a fine distortion change of, for example, about 0.2% to 1% occurs. Thus, although the method in which an examiner operates the ultrasonic probe 12 manually to press the object on the surface where ultrasonic waves are transmitted and received is advantageous in terms of being real time, simplicity, resolution, and cost, there is a problem that an elastic image suitable for diagnosis is not acquired if the pressure is not properly performed and this depends on the examiner's pressure technique.

Figure 2:
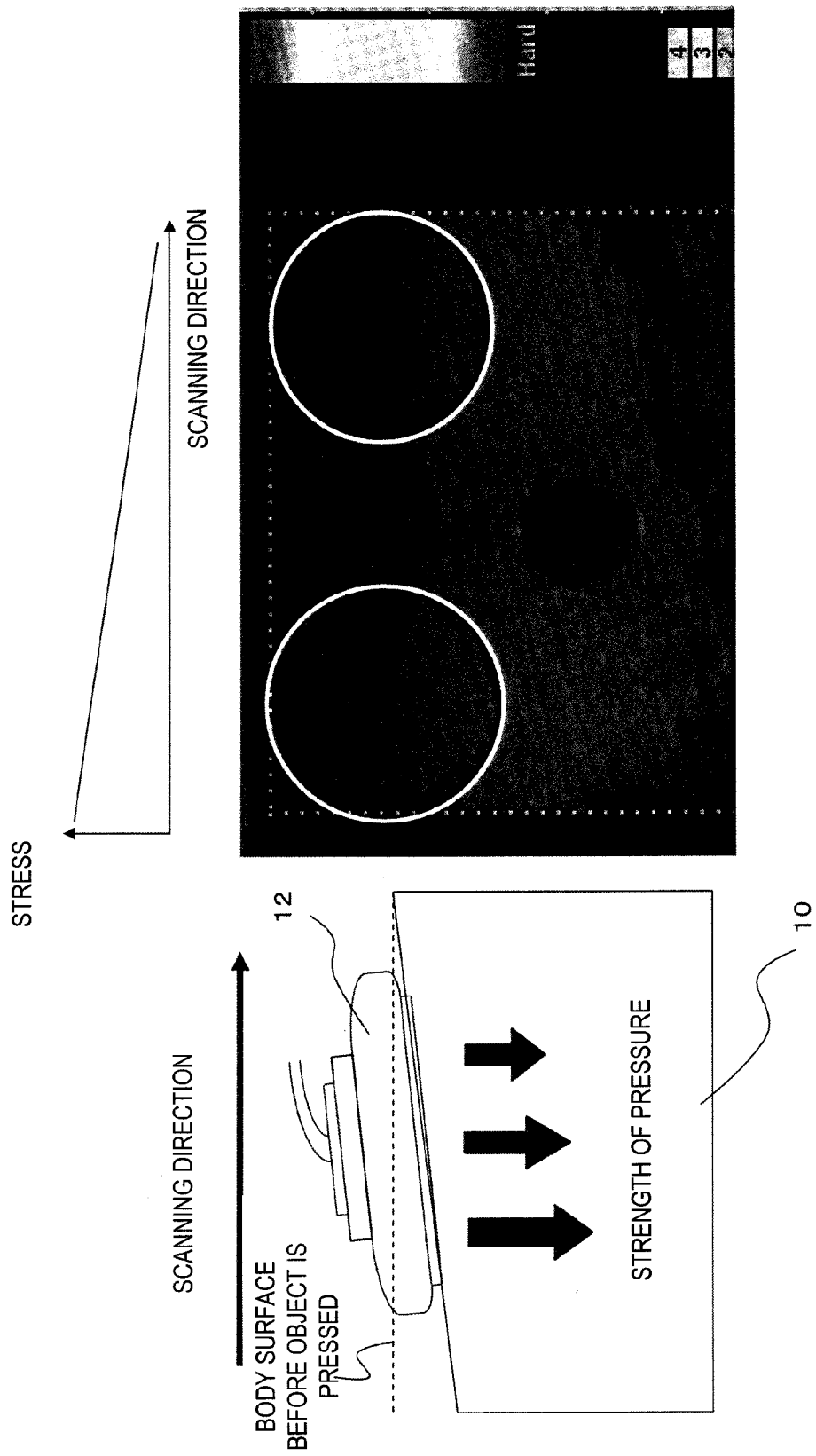
FIG. 2 is a view showing an example of an elastic image and the like at the time when the pressure technique is not proper.

FIG. 2 is a view showing an example of an elastic image and the like at the time when the pressure technique is not proper. As shown at the left side in FIG. 2, when the body surface before the object 10 is pressed (dotted line at the left side in FIG. 2) is pressed by the ultrasonic probe 12 in a state inclined along the scanning direction, tissue of the object 10 is unevenly pressed. As a result, the tissue of the object 10 is not uniformly pressed. In addition, the scanning direction is a direction perpendicular to the ultrasonic wave transmission and reception direction (direction along the body surface). The stress along the scanning direction is as shown in a graph on the upper right in FIG. 2. As a result, an elastic image in which tissue distortion in the scanning direction is not even is generated as shown at the lower right in FIG. 2. Since such an elastic image may not reflect the elasticity of a part to be diagnosed of the object 10 appropriately, it becomes an image which is not suitable for diagnosis.

In order to solve such a problem, the ultrasonic diagnostic apparatus 1 of the present embodiment includes the gradient detecting unit 40 provided to acquire an elastic image, which is suitable for diagnosis, easily without depending on the examiner's pressure technique and performs various kinds of processing according to the detection result of the gradient detecting unit 40. Hereinafter, details of the gradient detecting unit 40 which is a characteristic unit of the present embodiment will be described using each example.

Embodiment 1

Figure 3:
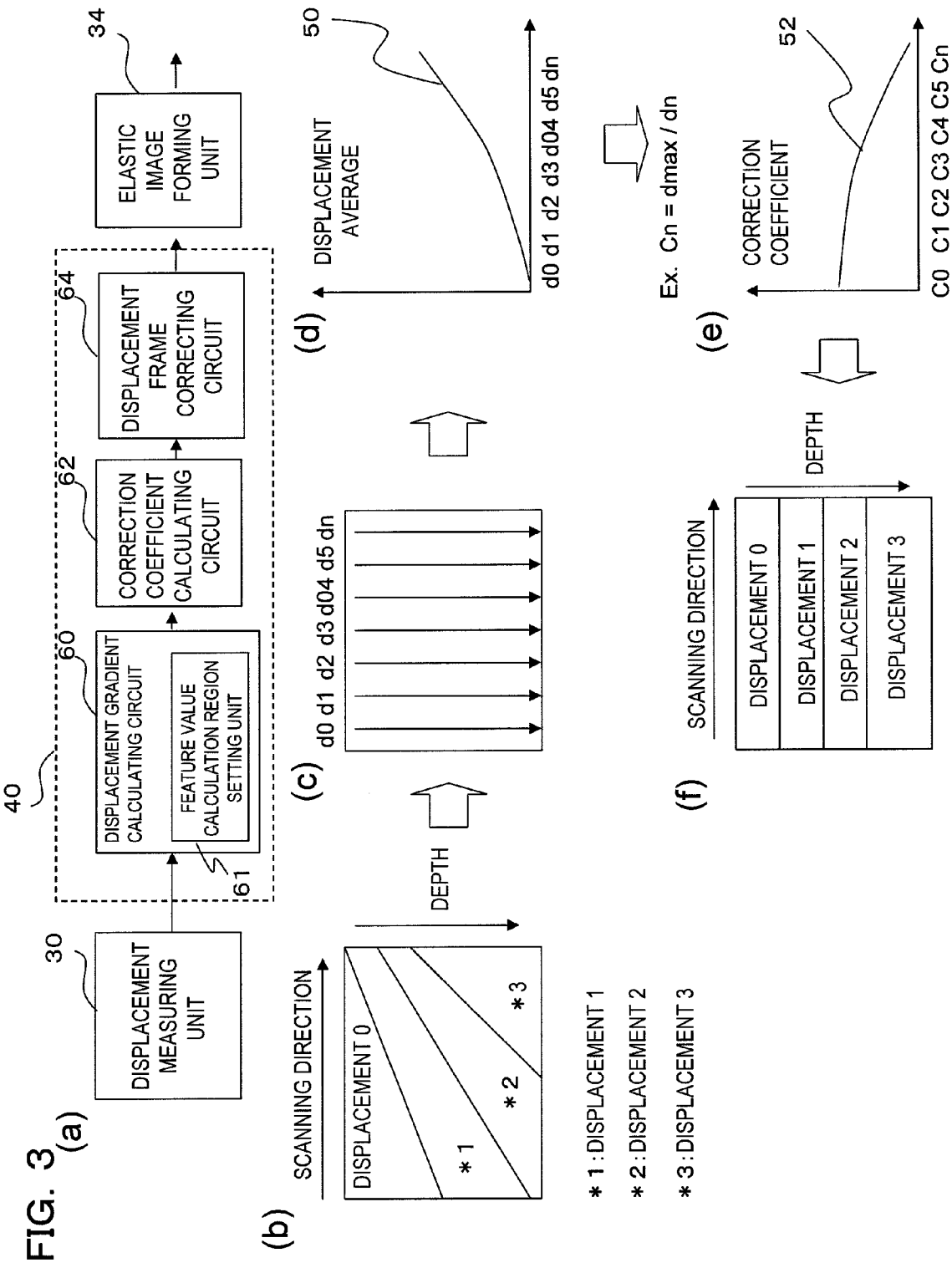
FIG. 3 is a view illustrating processing of a gradient detecting unit and the like in a first embodiment.

FIG. 3 is a view illustrating processing of the gradient detecting unit 40 and the like in a first embodiment. FIG. 3(a) is a view showing the detailed configuration of the gradient detecting unit 40. As shown in FIG. 3(a), the gradient detecting unit 40 is configured to include: a displacement gradient calculating circuit 60 which calculates a displacement gradient by calculating the average displacement of each beam line of the displacement frame output from the displacement measuring unit 30; a correction coefficient calculating circuit 62 which calculates a correction coefficient of each beam line on the basis of the calculated displacement gradient based on the average displacement or the like; and a displacement frame correcting circuit 64 which corrects a displacement frame on the basis of the correction coefficient. In addition, the displacement gradient calculating circuit 60 has a feature value calculation region setting unit 61 which sets a region where the feature value of displacement of each beam line of the displacement frame is calculated, and calculates a displacement gradient for the region set by the feature value calculation region setting unit 61. The displacement frame corrected by the displacement frame correcting circuit 64 is output to the elastic image forming unit 34.

Hereinafter, processing in the first embodiment which is executed by the displacement gradient calculating circuit 60, the correction coefficient calculating circuit 62, the displacement frame correcting circuit 64, and the like will be described. FIG. 3(b) schematically shows the distribution of the amount of displacement of tissue in a tomographic portion of the object between two frames. When the stress on the surface of the ultrasonic probe 12 is not uniform but uneven, the distribution of the amount of displacement of each beam line is not even as shown in FIG. 3(b). Therefore, the displacement gradient calculating circuit 60 calculates the feature value of displacement of each beam line by averaging, addition and subtraction, multiplication and division, square, and the like of the amount of displacement of each beam line (d0 to dN: N is a natural number), for example, a plurality of measurement points, as shown in FIG. 3(c). For example, when the average of the amount of displacement is arrayed as the displacement feature value as shown in FIG. 3(d), the feature value of displacement increases in a line in which large stress is applied and the feature value of displacement decreases in a line with small stress. The displacement gradient calculating circuit 60 calculates a displacement gradient 50 in the scanning direction of the ultrasonic probe 12 as shown in FIG. 3(d) by connecting the feature value of displacement of each beam line. In addition, it is assumed that tissue with almost uniform elasticity and tissue to be diagnosed, which has different elasticity from the tissue, are included in a tomographic portion of the object 10.

Then, the correction coefficient calculating circuit 62 calculates a correction coefficient 52 for the displacement of each beam line as shown in FIG. 3(e). The correction coefficient is a coefficient used to correct the inclination of the ultrasonic probe 12 along the scanning direction. That is, the correction coefficient is a coefficient for correcting the displacement measured when pressure of the ultrasonic probe 12 is given in a state inclined along the scanning direction. In other words, the correction coefficient is a coefficient for generating, in a pseudo manner, an elastic image at the time when pressure of an ultrasonic probe is given in a state where the ultrasonic probe is not inclined along the scanning direction. For example, the correction coefficient calculating circuit 62 can calculate the correction coefficient 52, like the "correction coefficient cN=dmax/dN", using the maximum value of the displacement average of scanning lines as a reference.

After the correction coefficient 52 is calculated, the displacement frame correcting circuit 64 generates an elastic image by correcting the displacement of each beam line on the basis of the correction coefficient 52 as shown in FIG. 3(f). For example, the displacement frame correcting circuit 64 can acquire the displacement after correction by multiplication of the correction coefficient 52 for each beam line and the amount of displacement of each line. In addition, the displacement frame correcting circuit 64 can generate an elastic image by performing image processing on the displacement frame, the elastic information frame, and the elastic frame data corrected by the elastic image forming unit 34 on the basis of the correction coefficient 52 and giving the color information to the elastic frame data using the color scan converter 36. Moreover, although the displacement gradient based on displacement is calculated in this example, gradients based on parameters, such as distortion, elastic modulus, and viscosity depending on the displacement, are also included in the displacement gradient.

According to this example, an elastic image generated in a pseudo manner when the ultrasonic probe 12 presses the object 10 in a state not inclined even if the ultrasonic probe 12 presses the object 10 in a state inclined along the scanning direction, since the correction coefficient calculating circuit 62 calculates a correction coefficient for correcting the inclination of the ultrasonic probe 12 on the basis of the displacement gradient in the scanning direction and the displacement frame correcting circuit 64 corrects an elastic image on the basis of the correction coefficient. As a result, the examiner can acquire an elastic image suitable for diagnosis easily without depending on the examiner's pressure technique.

Embodiment 2

Figure 4:
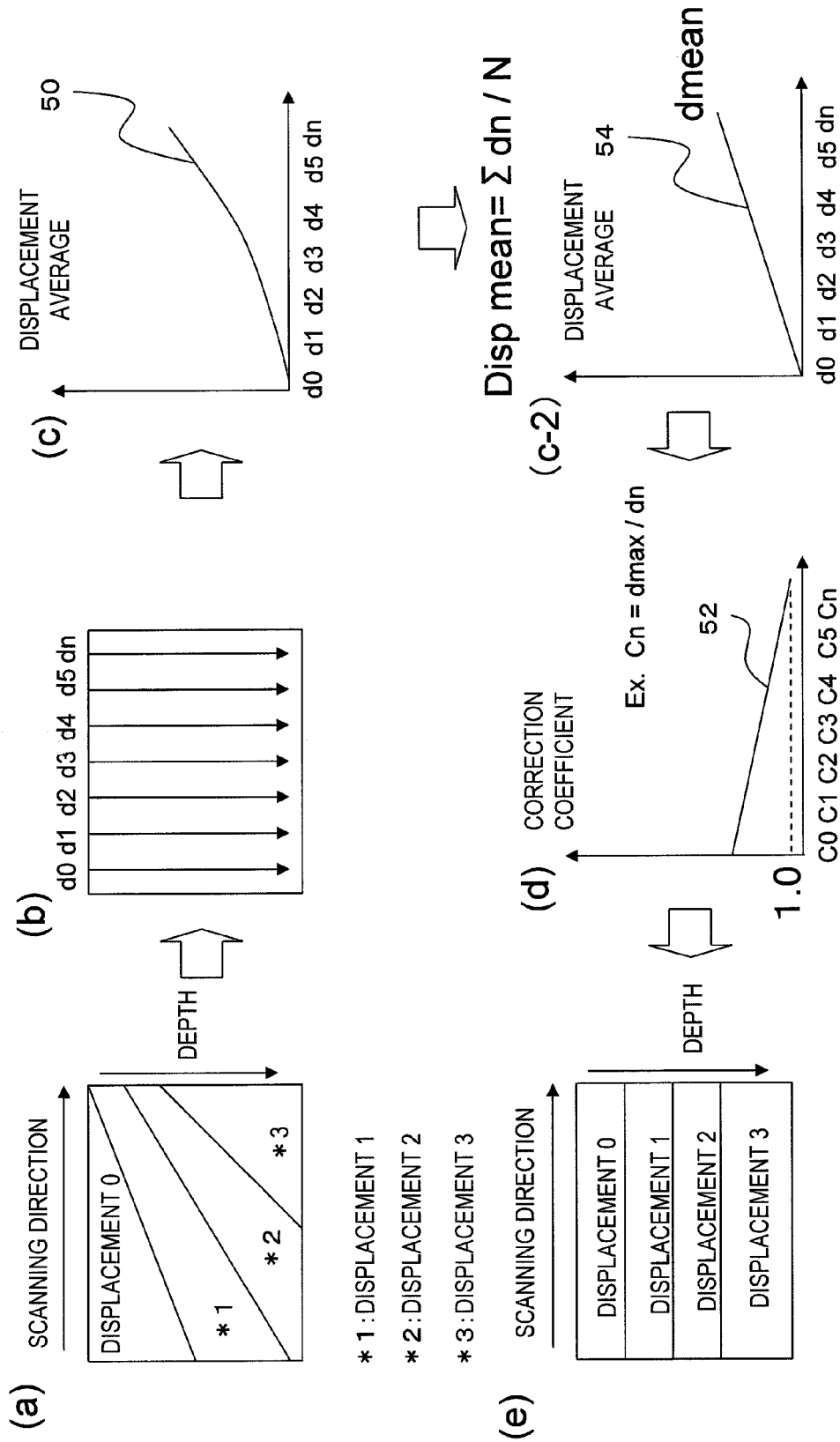
FIG. 4 is a view illustrating processing of a gradient detecting unit and the like in a second embodiment.

FIG. 4 is a view illustrating processing of the gradient detecting unit 40 and the like in a second embodiment. The detailed configuration of the gradient detecting unit 40 is the same as that in the first embodiment. Hereinafter, processing in the second embodiment which is executed by the displacement gradient calculating circuit 60, the correction coefficient calculating circuit 62, the displacement frame correcting circuit 64, and the like will be described. In addition, explanation regarding the same units as in the first embodiment will be omitted. In this example, the displacement gradient calculating circuit 60 calculates the displacement gradient 50 as shown in FIG. 4(c) and then corrects the displacement gradient on the basis of the average of the feature value of displacement of each beam line as shown in FIG. 4(c-2). For example, the displacement gradient calculating circuit 60 calculates the average (Disp mean) of the displacement feature value of each beam line by Disp mean=$\Sigma$dn/N (N: the number of beam lines), sets the calculated average value of the displacement feature value as dmean, and sets it as a displacement feature value corresponding to the beam line dn. Then, dmean and the displacement feature value 0 corresponding to the beam line d0 are connected to each other with a straight line, and this is set as a corrected displacement gradient 54.

After correcting the displacement gradient, the correction coefficient calculating circuit 62 calculates the correction coefficient 52 for each beam line and the displacement frame correcting circuit 64 corrects the displacement of each beam line on the basis of the correction coefficient 52 to thereby generate an elastic image, as in the first embodiment. According to this example, for example, even if tissue with different elasticity is somewhat included in tissue with uniform elasticity, a stable displacement gradient can be acquired without an influence of the tissue. As a result, the inclination of the ultrasonic probe 12 can be calculated more accurately.

Embodiment 3

Figure 5:
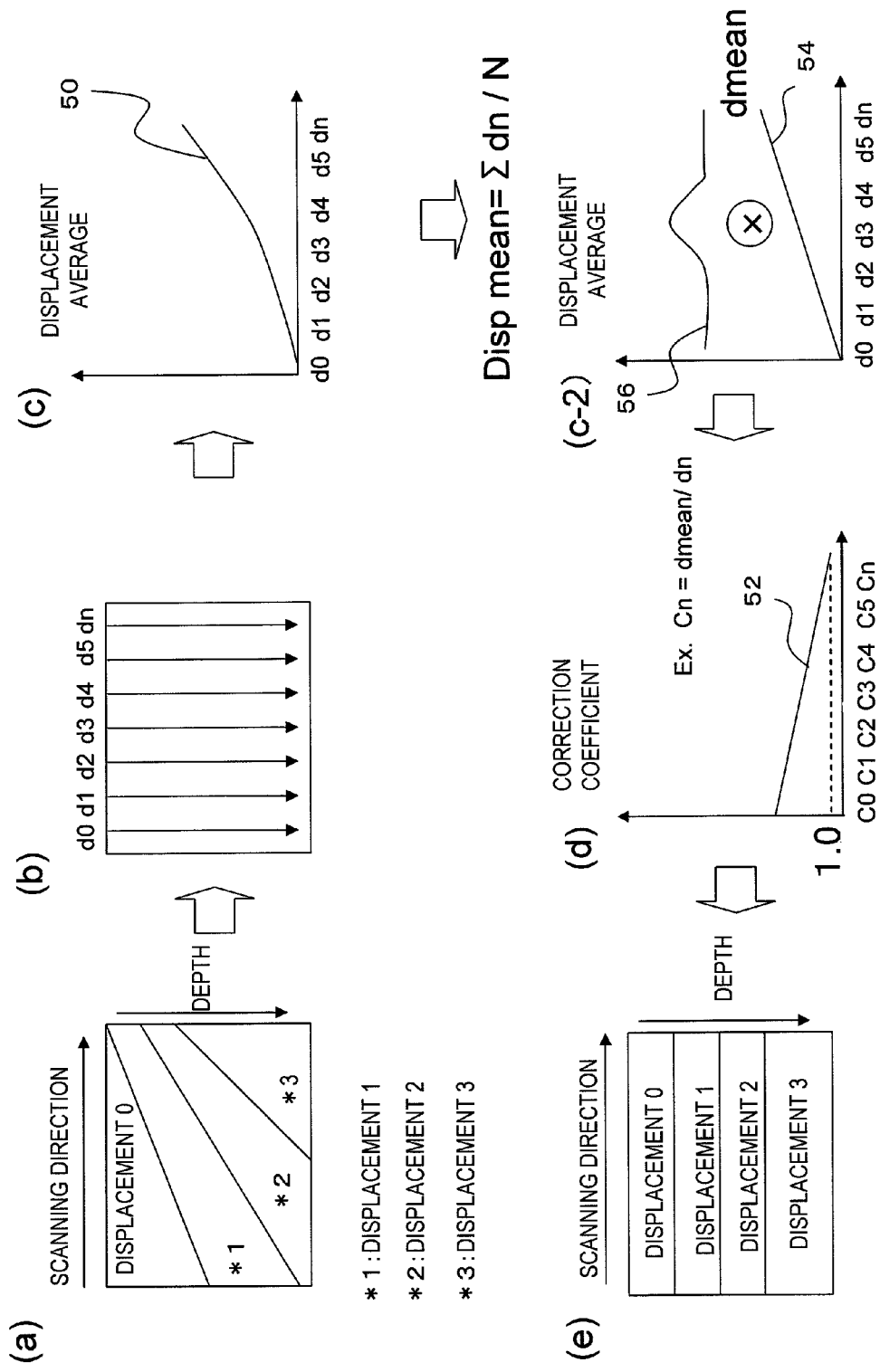
FIG. 5 is a view illustrating processing of a gradient detecting unit and the like in a third embodiment.

FIG. 5 is a view illustrating processing of the gradient detecting unit 40 and the like in a third embodiment. The detailed configuration of the gradient detecting unit 40 is the same as that in the first embodiment. Hereinafter, processing in the third embodiment which is executed by the displacement gradient calculating circuit 60, the correction coefficient calculating circuit 62, the displacement frame correcting circuit 64, and the like will be described. In addition, explanation on the same unit as in the first and second embodiments will be omitted. In this example, the displacement gradient calculating circuit 60 calculates the displacement gradient 54 corrected as shown in FIG. 5(*c*-2) and then corrects this displacement gradient further on the basis of a stress distribution coefficient 56 in the scanning direction of an ultrasonic probe set in advance. For example, the displacement gradient calculating circuit 60 calculates a displacement gradient by multiplying the corrected displacement gradient 54 by the stress distribution coefficient 56 in the scanning direction of the ultrasonic probe set in advance. In addition, the displacement gradient calculating circuit 60 may also correct the displacement gradient 50 calculated in the first embodiment by multiplying the displacement gradient 50 by the stress distribution coefficient 56.

After correcting the displacement gradient, the correction coefficient calculating circuit 62 calculates the correction coefficient 52 for each beam line and the displacement frame correcting circuit 64 corrects the displacement of each beam line on the basis of the correction coefficient to thereby generate an elastic image, as in the first embodiment. According to this example, it is possible to improve the accuracy of a correction coefficient in consideration of the characteristic of the stress distribution at the time when the ultrasonic probe 12 presses the object.

That is, at both ends of the ultrasonic probe 12 in the scanning direction, stress at the time when the object is pressed tends to be distributed outside from both the pressed ends of the object. Accordingly, the stress distribution tends to be convex along the scanning direction. Therefore, the stress distribution coefficient 56 in the scanning direction of the ultrasonic probe 12 is calculated in advance by an experiment or simulation and set in the ultrasonic diagnostic apparatus, the displacement gradient in the scanning direction is corrected on the basis of the stress distribution coefficient by the displacement gradient calculating circuit 60, and the correction coefficient is calculated on the basis of the displacement gradient corrected by the correction coefficient calculating circuit 62. As a result, the accuracy of the correction coefficient can be improved.

Embodiment 4

Figure 6:
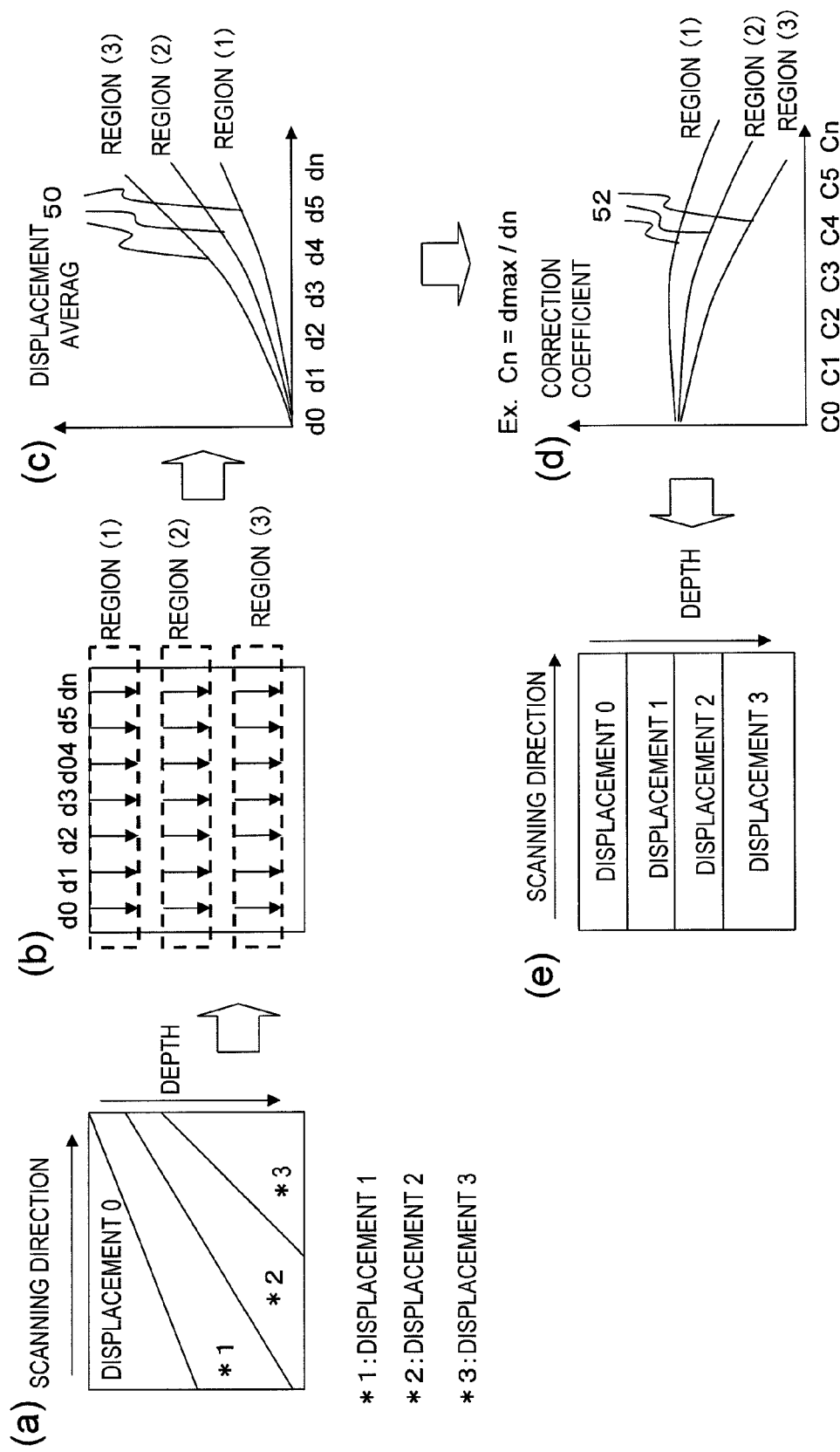
FIG. 6 is a view illustrating processing of a gradient detecting unit and the like in a fourth embodiment.

FIG. 6 is a view illustrating processing of the gradient detecting unit 40 and the like in a fourth embodiment. The detailed configuration of the gradient detecting unit 40 is the same as that in the first embodiment. Hereinafter, processing in the fourth embodiment which is executed by the displacement gradient calculating circuit 60, the correction coefficient calculating circuit 62, the displacement frame correcting circuit 64, and the like will be described. In addition, explanation regarding the same units as in the first embodiment and the like will be omitted. In the first to third embodiments, the case has been exemplified in which the feature value calculation region setting unit 61 sets all displacement frames in a tomographic portion of the object as a feature value calculation region. In this example, however, as shown in FIG. 6(*b*), a feature value calculation region at the time when the feature value calculation region setting unit 61 calculates a feature value of displacement is set by division into a plurality of regions in the depth direction. In other words, the feature value calculation region setting unit 61 sets a plurality of feature value calculation regions (regions of interest) along the depth direction of the beam line of an ultrasonic wave, and the displacement gradient calculating circuit 60 calculates a displacement feature value for each feature value calculation region to calculate the displacement gradient 50.

In this example, the feature value calculation region setting unit 61 sets, for example, three regions (1) to (3) in the depth direction of an ultrasonic beam as shown in FIG. 6(*b*), and the displacement gradient calculating circuit 60 calculates the displacement gradient 50 for each of the regions (1) to (3) as shown in FIG. 6(*c*). In addition, the correction coefficient calculating circuit 62 calculates the correction coefficient 52 for each of the regions (1) to (3) as shown in FIG. 6(*d*) and the displacement frame correcting circuit 64 corrects the displacement of each beam line in each corresponding region on the basis of each correction coefficient to thereby generate an elastic image. For example, if several organs with different elasticity are included in the depth direction of an ultrasonic beam, the displacement distribution becomes complicated. As a result, appropriate correction of an elastic image may not be performed. In regard to this point, according to this example, appropriate correction can be performed for an elastic image since a displacement gradient or a correction coefficient is calculated for each tissue with approximately uniform elastic Embodiment 5

Figure 7:
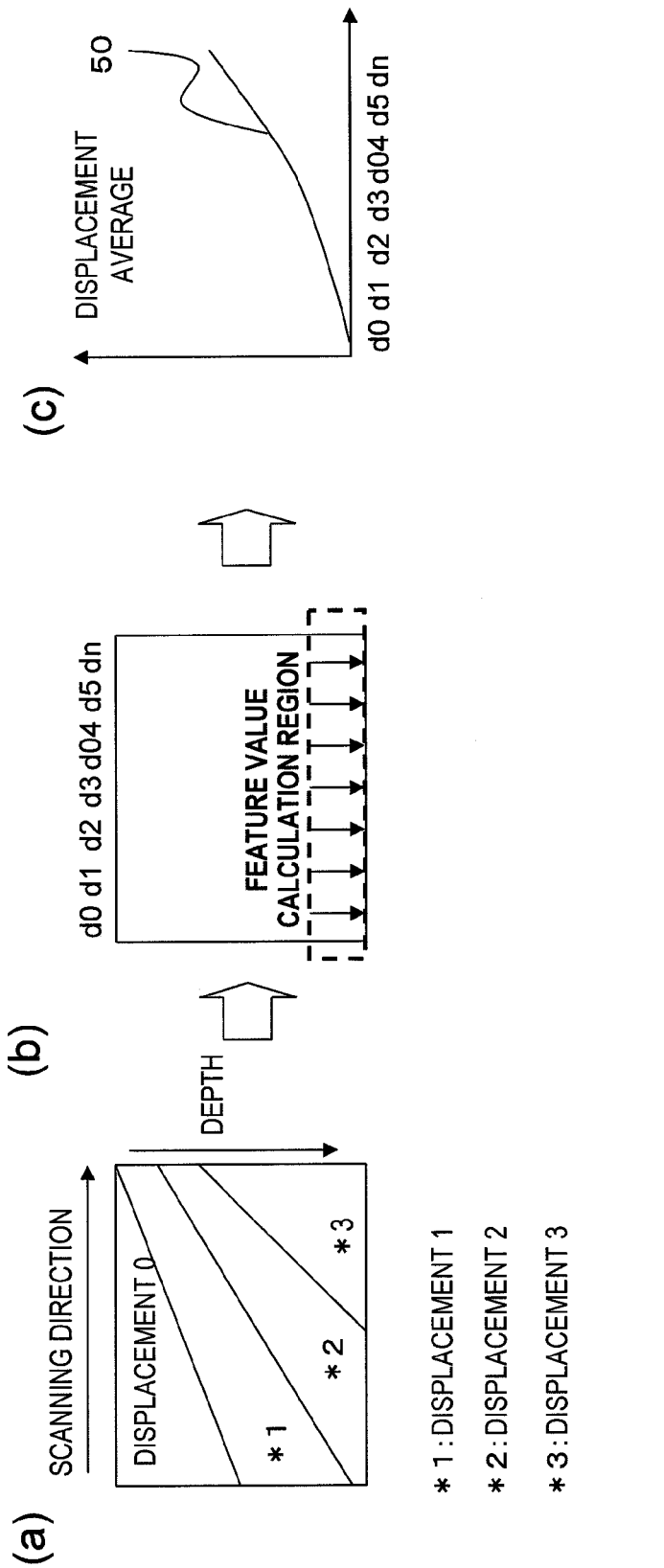
FIG. 7 is a view illustrating processing of a gradient detecting unit and the like in a fifth embodiment.

FIG. 7 is a view illustrating processing of the gradient detecting unit 40 and the like in a fifth embodiment. The detailed configuration of the gradient detecting unit 40 is the same as that in the first embodiment. Hereinafter, processing in the fifth embodiment which is executed by the displacement gradient calculating circuit 60, the correction coefficient calculating circuit 62, the displacement frame correcting circuit 64, and the like will be described. In addition, explanation regarding the same units as in the first embodiment and the like will be omitted. In this example, the feature value calculation region setting unit 61 sets a feature value calculation region in a part in the depth direction of the beam line of an ultrasonic wave as shown in FIG. 7(*b*) and the displacement gradient calculating circuit 60 calculates a displacement feature value for this feature value calculation region to thereby calculate the displacement gradient 50. Processing after calculating the displacement gradient 50 is the same as that in the first embodiment and the like. In addition, an examiner may input and set a feature value calculation region arbitrarily through the interface unit 42, or the feature value calculation region setting unit 61 may set a feature value calculation region automatically according to the elasticity of tissue in a tomographic portion of the object. For example, the feature value calculation region setting unit 61 sets a plurality of candidate regions, among feature value calculation regions (regions of interest), along the depth direction of the beam line of an ultrasonic wave in a tomographic portion of the object, calculates a variation in the elasticity (displacement, distortion, an elastic modulus, and the like) of tissue in each of the plurality of candidate regions, and sets the candidate region with the smallest variation as a feature value calculation region.

According to this example, for example, when tissue with different elasticity is mixed in an upper portion of the tomographic portion of the object, the feature value calculation region setting unit 61 sets a feature value calculation region only in a lower portion with uniform elasticity, so that the displacement gradient calculating circuit 60 can calculate a degree of inclination (displacement gradient) of the ultrasonic probe 12 more accurately. As a result, since the correction coefficient calculating circuit 62 can obtain an appropriate correction coefficient, the displacement frame correcting circuit 64 can correct an elastic image more accurately.

Embodiment 6

Figure 8:
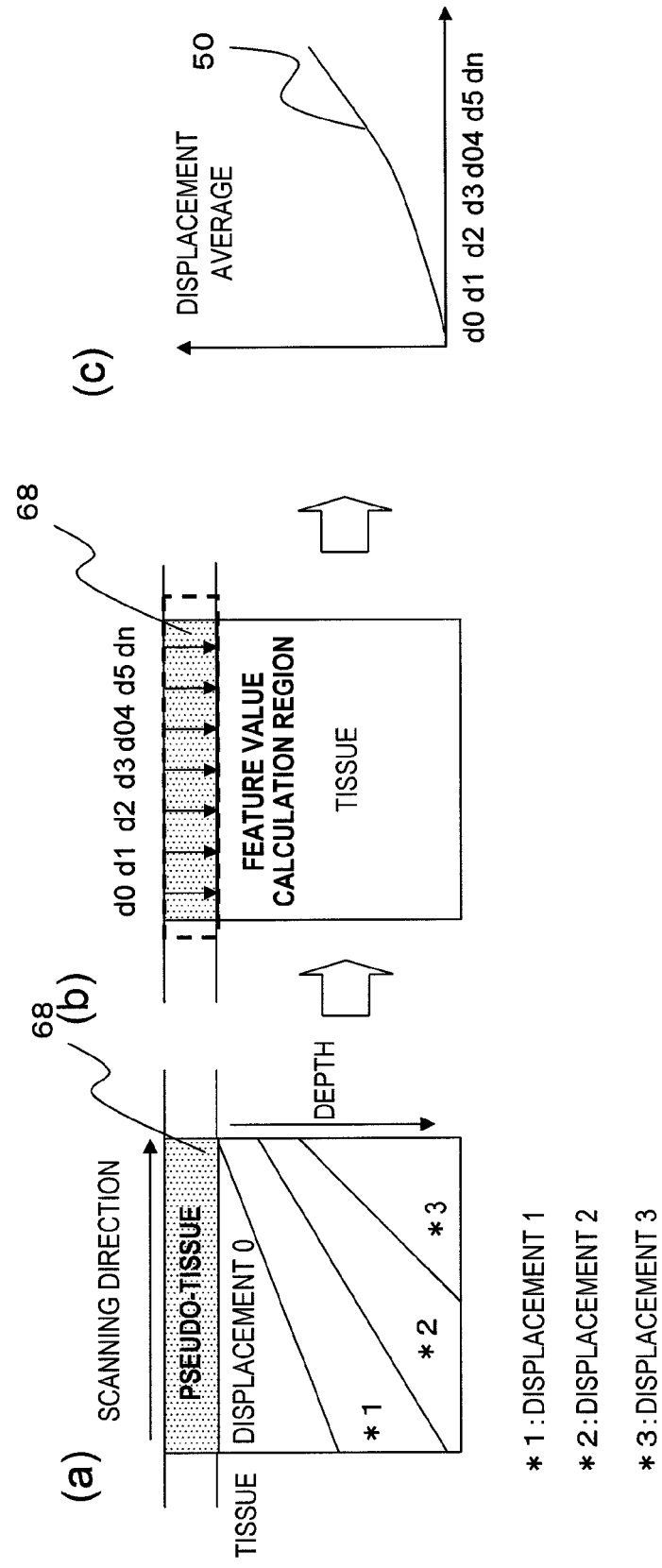
FIG. 8 is a view illustrating processing of a gradient detecting unit and the like in a sixth embodiment.

FIG. 8 is a view illustrating processing of the gradient detecting unit 40 and the like in a sixth embodiment. The detailed configuration of the gradient detecting unit 40 is the same as that in the first embodiment. Hereinafter, processing in the sixth embodiment which is executed by the displacement gradient calculating circuit 60, the correction coefficient calculating circuit 62, the displacement frame correcting circuit 64, and the like will be described. In addition, explanation regarding the same units as in the first embodiment and the like will be omitted. In this example, the feature value calculation region setting unit 61 sets a feature value calculation region to pseudo-tissue 68 as shown in FIG. 8(b) and the displacement gradient calculating circuit 60 calculates a displacement feature value for this feature value calculation region to thereby calculate the displacement gradient 50.

In addition, the pseudo-tissue 68 is provided on the ultrasonic wave transmission and reception surface of the ultrasonic probe 12, has uniform elasticity, and is known.

According to this example, using the known pseudo-tissue with uniform elasticity, the displacement gradient calculating circuit 60 can more accurately calculate the inclination (displacement gradient) of the ultrasonic probe 12 along the scanning direction occurring due to the examiner's pressure technique. As a result, since the correction coefficient calculating circuit 62 can obtain an appropriate correction coefficient, the displacement frame correcting circuit 64 can correct an elastic image more accurately.

Figure 9:
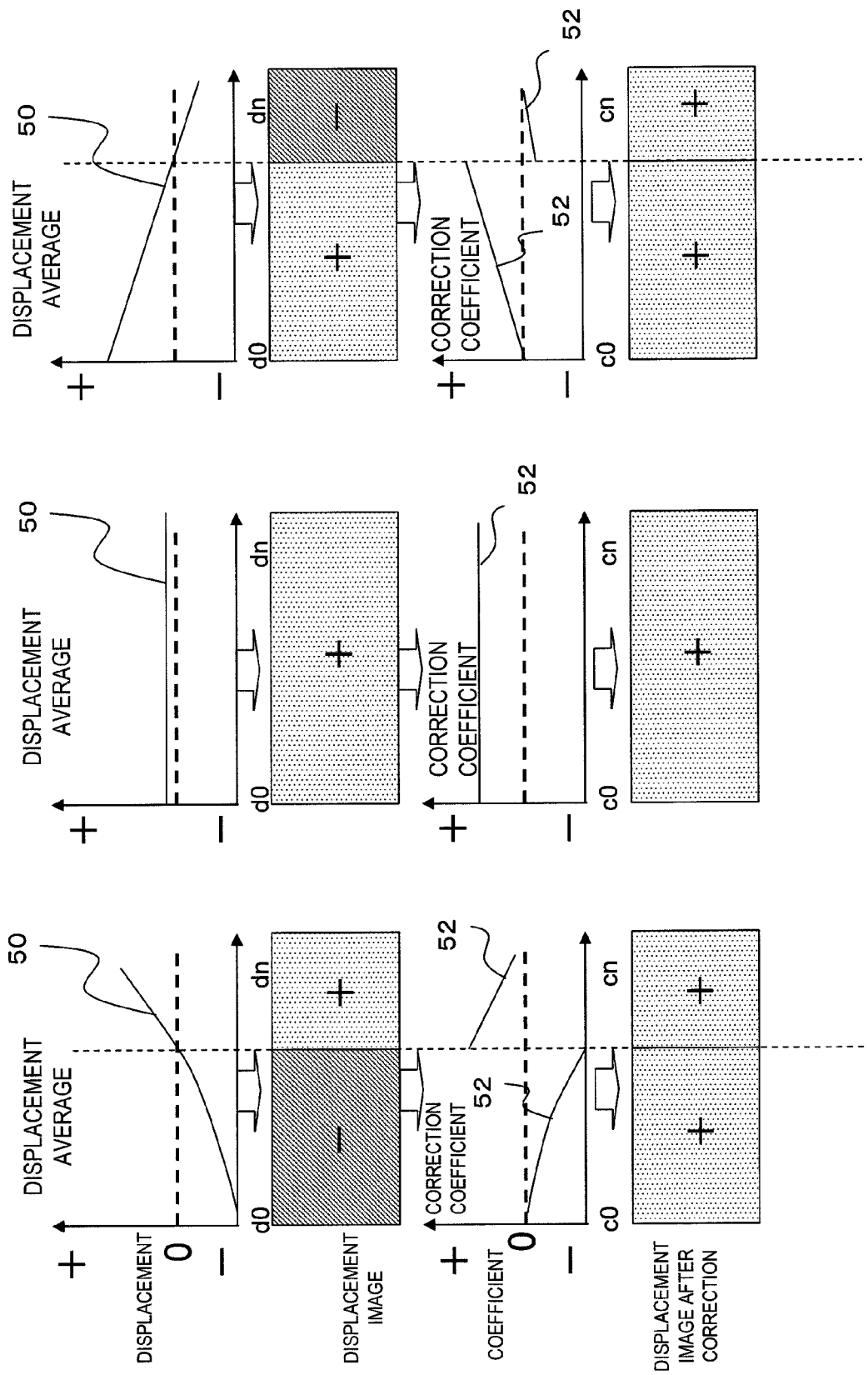
FIG. 9 is a view showing an example of a method of calculating a correction coefficient when the displacement is positive and negative and when the displacement is only positive.
Figure 10:
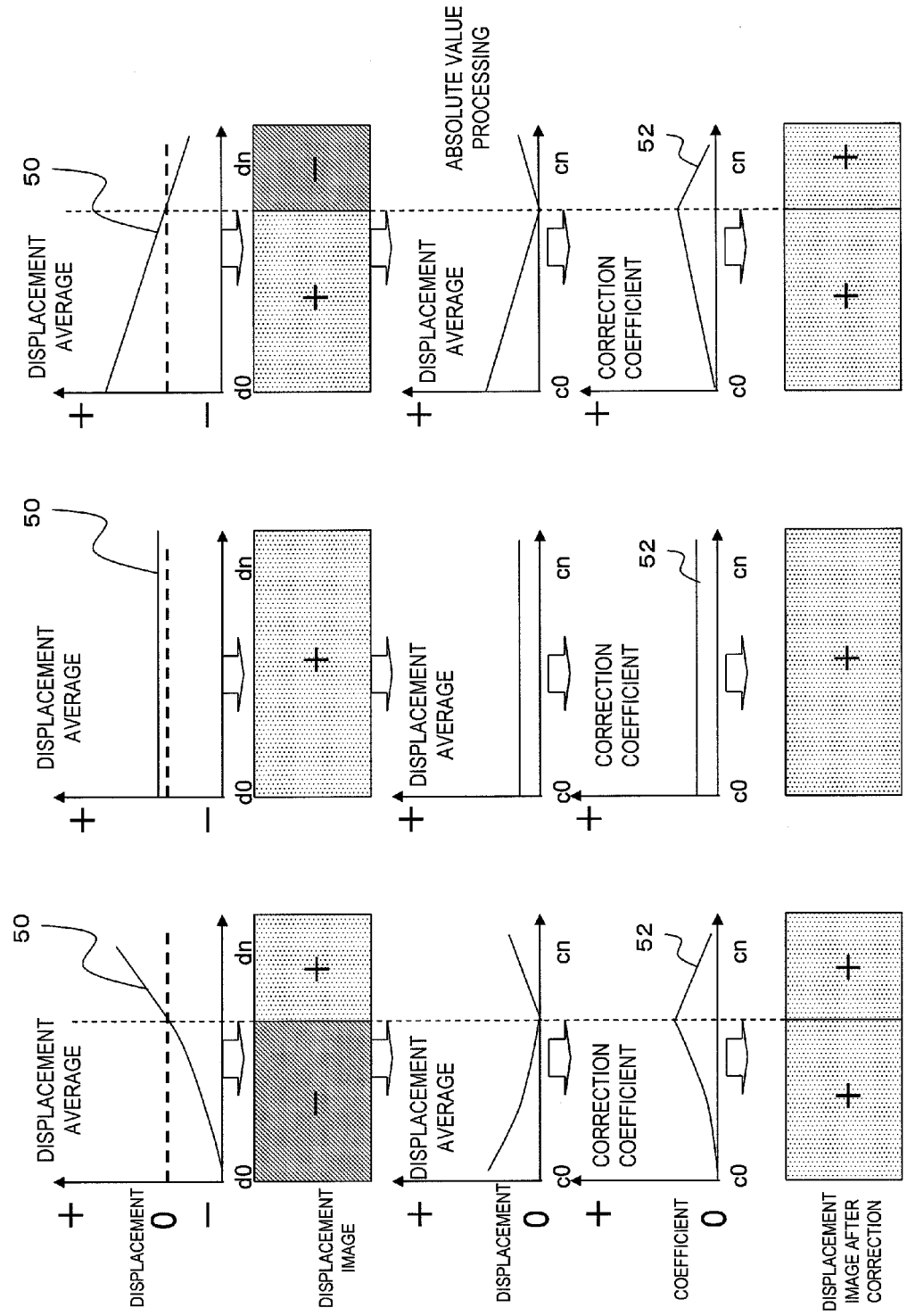
FIG. 10 is a view showing an example of a method of calculating a correction coefficient when the displacement is positive and negative and when the displacement is only positive.

In addition, although each of the above examples has been described on the assumption that the displacement of tissue of each beam line is positive displacement in the scanning direction, the correction coefficient calculating circuit 62 may also calculate a correction coefficient in the same way in cases where the displacement is positive and negative in the scanning direction. For example, FIG. 9 shows an example of a method of calculating a correction coefficient when the displacement is positive and negative and when the displacement is only positive. As shown in FIG. 9, when there is a negative displacement, the correction coefficient calculating circuit 62 can perform appropriate correction in the same manner as the case where the displacement is only positive by calculating the correction coefficient according to the negative displacement. In addition, FIG. 10 shows an example of a method of calculating a correction coefficient when the displacement is positive and negative and when the displacement is only positive. As shown in FIG. 10, when there is a negative displacement, the correction coefficient calculating circuit 62 can perform appropriate correction like the case of only positive displacement by performing absolute value processing on the negative portion.

Embodiment 7

Figure 11:
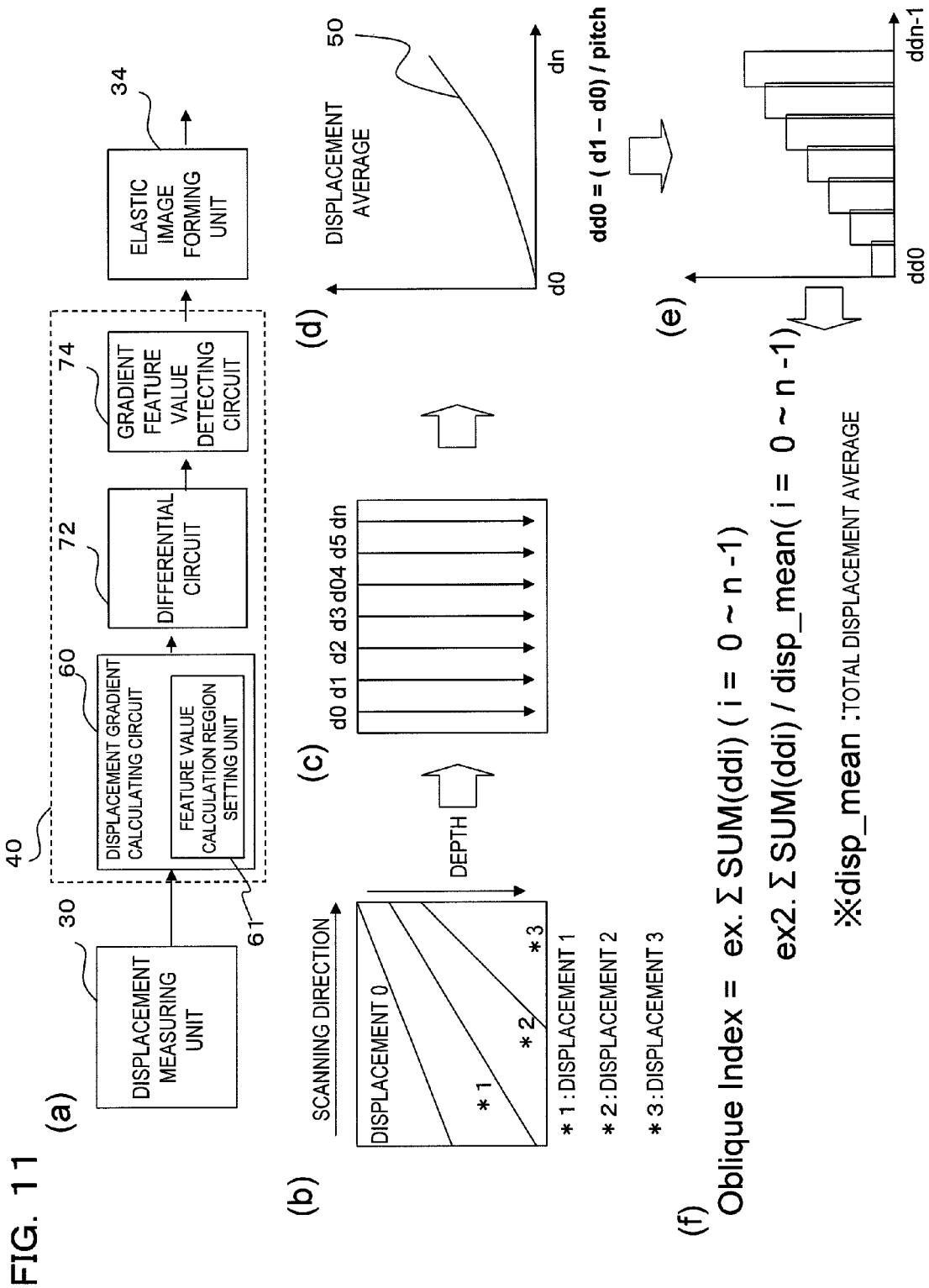
FIG. 11 is a view illustrating processing of a gradient detecting unit and the like in a seventh embodiment.
Figure 12:
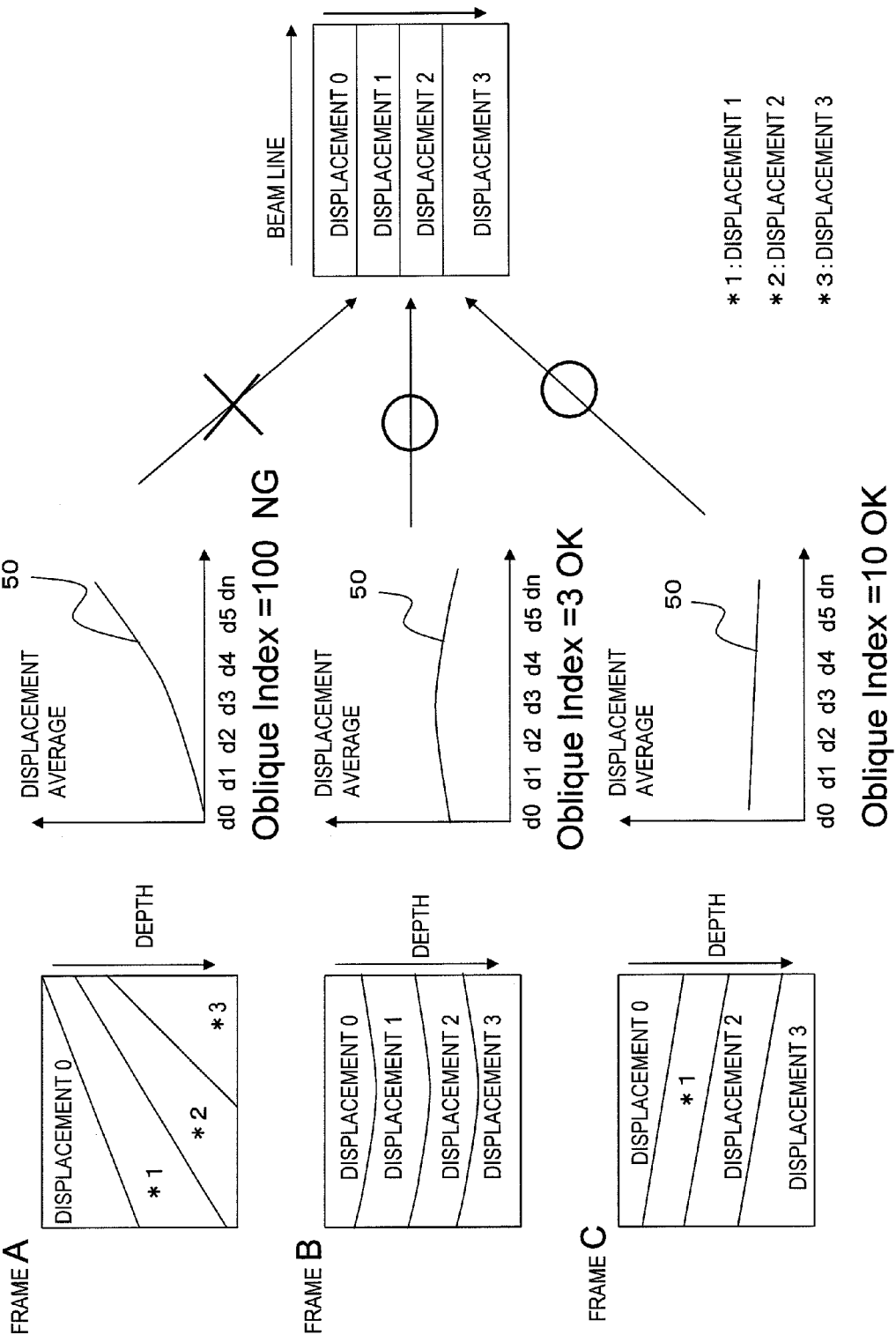
FIG. 12 is a view illustrating processing of a gradient detecting unit and the like in the seventh embodiment.

FIGS. 11 and 12 are views illustrating processing of the gradient detecting unit 40 and the like in a seventh embodiment. As shown in FIG. 11(a), the gradient detecting unit 40 in this example is configured to include: a displacement gradient calculating circuit 60 which calculates a displacement gradient by calculating the average displacement of each beam line of the displacement frame output from the displacement measuring unit 30; a differential circuit 72 which differentiates the average displacement of each beam line between lines; and a gradient feature value detecting circuit 74 which calculates the feature value of a displacement gradient. The calculated feature value of the displacement gradient is output to the elastic image forming unit 34 or the like, for example. In addition, explanation regarding the same units as in the first embodiment and the like will be omitted. In this example, the displacement gradient calculating circuit 60 calculates a displacement gradient in a scanning direction for each frame of displacement of tissue in a tomographic portion of the object, the differential circuit 72 and the gradient feature value detecting circuit 74 calculate the feature value of a displacement gradient on the basis of the calculated displacement gradient, and the image mixing unit 38 selects and mixes a plurality of displacement frames of which feature values of displacement gradients are smaller than the threshold value set in advance.

FIG. 11 is a view showing an example of calculating the feature value of a displacement gradient. This is the same as the first embodiment and the like until the displacement gradient 50 is calculated by the displacement gradient calculating circuit 60, as shown in FIG. 11(d). In this example, the differential circuit 72 calculates the amount of increase or decrease shown in FIG. 11(e) by differentiating the feature value of displacement of each beam line between lines. For example, the amount of increase or decrease between beam lines d0 and d1 is calculated by dd0=(d1−d0)/pitch. The pitch is a distance between beam lines.

In addition, as shown in FIG. 11(f), the gradient feature value detecting circuit 74 calculates a feature value (Oblique Index) of the displacement gradient with the start point of a beam as a reference by adding values of increase or decrease in the displacement between lines, for example. That is, Oblique Index=ΣSUM(ddi) (i=0 to N-1). In addition, the gradient feature value detecting circuit 74 may also set the averaging of values of increase or decrease of displacement between lines as a feature value of the displacement gradient, for example. That is, Oblique Index=ΣSUM(ddi)/diSp_meaN (i=0 to N-1). Disp mean is the total displacement average.

FIG. 12 is a view showing an example in which the image mixing unit 38 selects and mixes a plurality of displacement frames or the like on the basis of a feature value of the displacement gradient. As shown in FIG. 12, there is a plurality of displacement frames A, B, and C acquired at different times, and feature values (Oblique Index) of displacement gradients thereof are assumed to be 100, 3, and 10, respectively. In addition, the threshold value set in advance in order to sort out the displacement frames is assumed to be 15. In this case, the image mixing unit 38 selects only the displacement frames B and C with the feature values of displacement gradients, which are smaller than the threshold value set in advance, and executes mixing processing (smoothing processing), which is represented by persistence processing, on the displacement frames B and C.

According to the present example, since the image mixing unit 38 selects and mixes only good frames with smaller displacement gradient feature values than the threshold value set in advance, that is, only good frames obtained by pressing the object in a state where the inclination of the ultrasonic probe 12 along the scanning direction is allowable, it is possible to obtain an elastic image with higher accuracy. In addition, the image mixing unit 38 may perform mixing processing not only on displacement frames but also on a plurality of elastic information frames based on a plurality of displacement frames with smaller displacement gradient feature values than the threshold value set in advance or a plurality of elastic image frames based on a plurality of displacement frames with smaller displacement gradient feature values than the threshold value set in advance.

In addition, the threshold value of the displacement gradient feature value may be set in advance in an ultrasonic diagnostic apparatus, for example, for each part to be diagnosed, such as a mammary gland, a thyroid gland, or a prostate gland, or may be input or changed and set through the interface unit 42 by the examiner.

Embodiment 8

Figure 13:
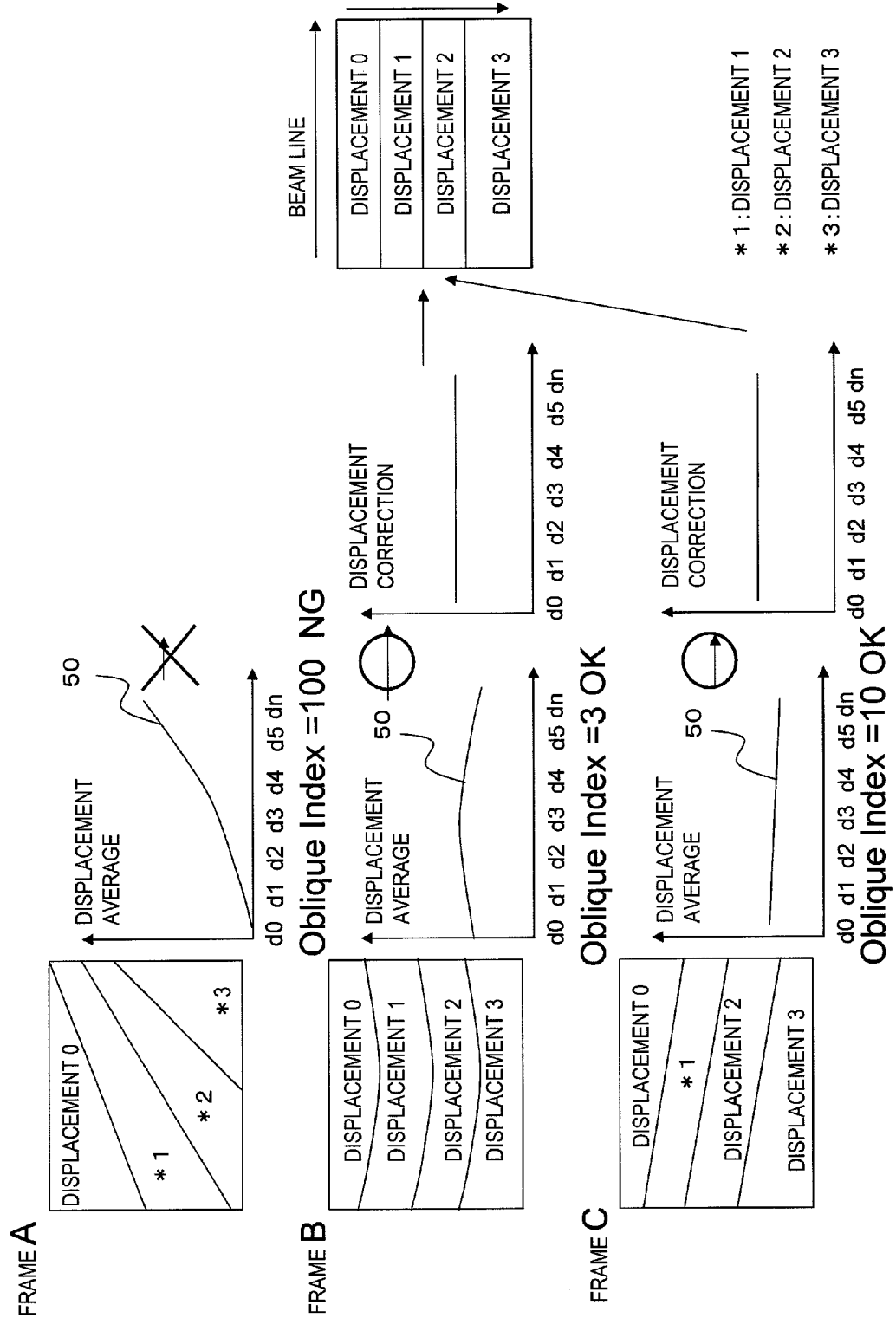
FIG. 13 is a view illustrating processing of a gradient detecting unit and the like in an eighth embodiment.

FIG. 13 is a view illustrating processing of the gradient detecting unit 40 and the like in an eighth embodiment. The detailed configuration of the gradient detecting unit 40 is the same as that in the seventh embodiment. Hereinafter, processing in the eighth embodiment which is executed by the displacement gradient calculating circuit 60, the differential circuit 72, the gradient feature value detecting circuit 74, the image mixing unit 38, the correction coefficient calculating circuit 62, the displacement frame correcting circuit 64, and the like will be described. In addition, explanation regarding the same units as in the first and seventh embodiments and the like will be omitted. In this example, the image mixing unit 38 selects a plurality of displacement frames with smaller displacement gradient feature values than the threshold value set up in advance, the displacement frame correcting circuit 64 corrects each of the plurality of selected displacement frames on the basis of a correction coefficient, and the image mixing unit 38 mixes the plurality of corrected displacement frames and the like.

As shown in FIG. 13, there is a plurality of displacement frames A, B, and C acquired at different times, and feature values (Oblique Index) of displacement gradients thereof are assumed to be 100, 3, and 10, respectively. In addition, the threshold value set in advance in order to sort out the displacement frames is assumed to be 15. In this case, the image mixing unit 38 selects only the displacement frames B and C with smaller feature values of displacement gradients than the threshold value set in advance. The displacement frame correcting circuit 64 corrects the displacement frames B and C on the basis of the correction coefficient 52. In addition, the image mixing unit 38 executes mixing processing (smoothing processing), which is represented by persistence processing, on the corrected displacement frames B and C.

According to this example, the image mixing unit 38 selects only good frames obtained by pressing the object in a state where the inclination of an ultrasonic probe along the scanning direction is allowable, the displacement frame correcting circuit 64 corrects them on the basis of a correction coefficient in a pseudo manner in a state where there is no inclination, and the image mixing unit 38 mixes them. As a result, the accuracy of an elastic image can be further improved. In addition, the image mixing unit 38 may select and mix a plurality of elastic information frames based on a plurality of corrected displacement frames or a plurality of elastic image frames based on a plurality of corrected displacement frames.

Embodiment 9

Figure 14:
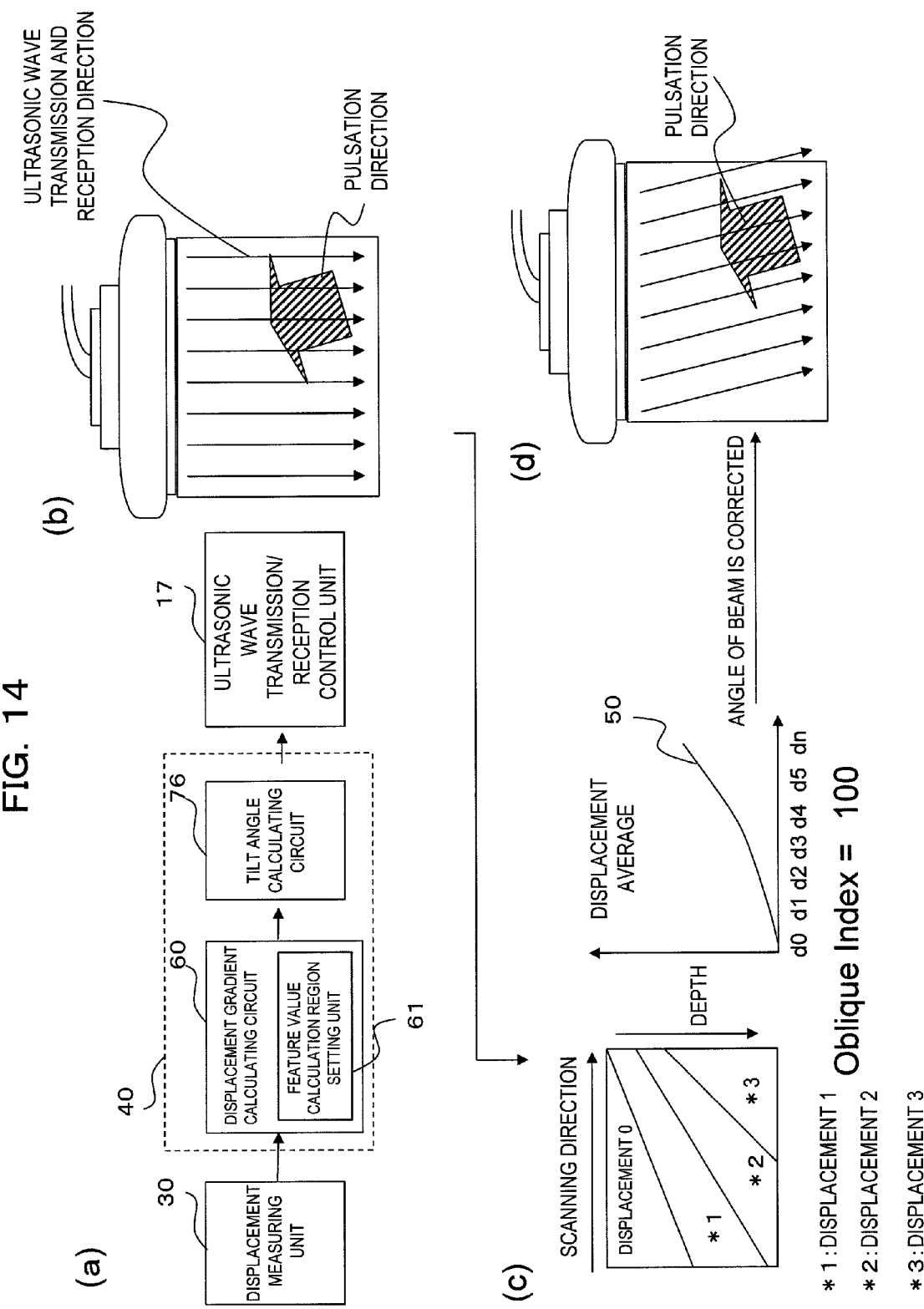
FIG. 14 is a view illustrating processing of a gradient detecting unit and the like in a ninth embodiment.
Figure 15:
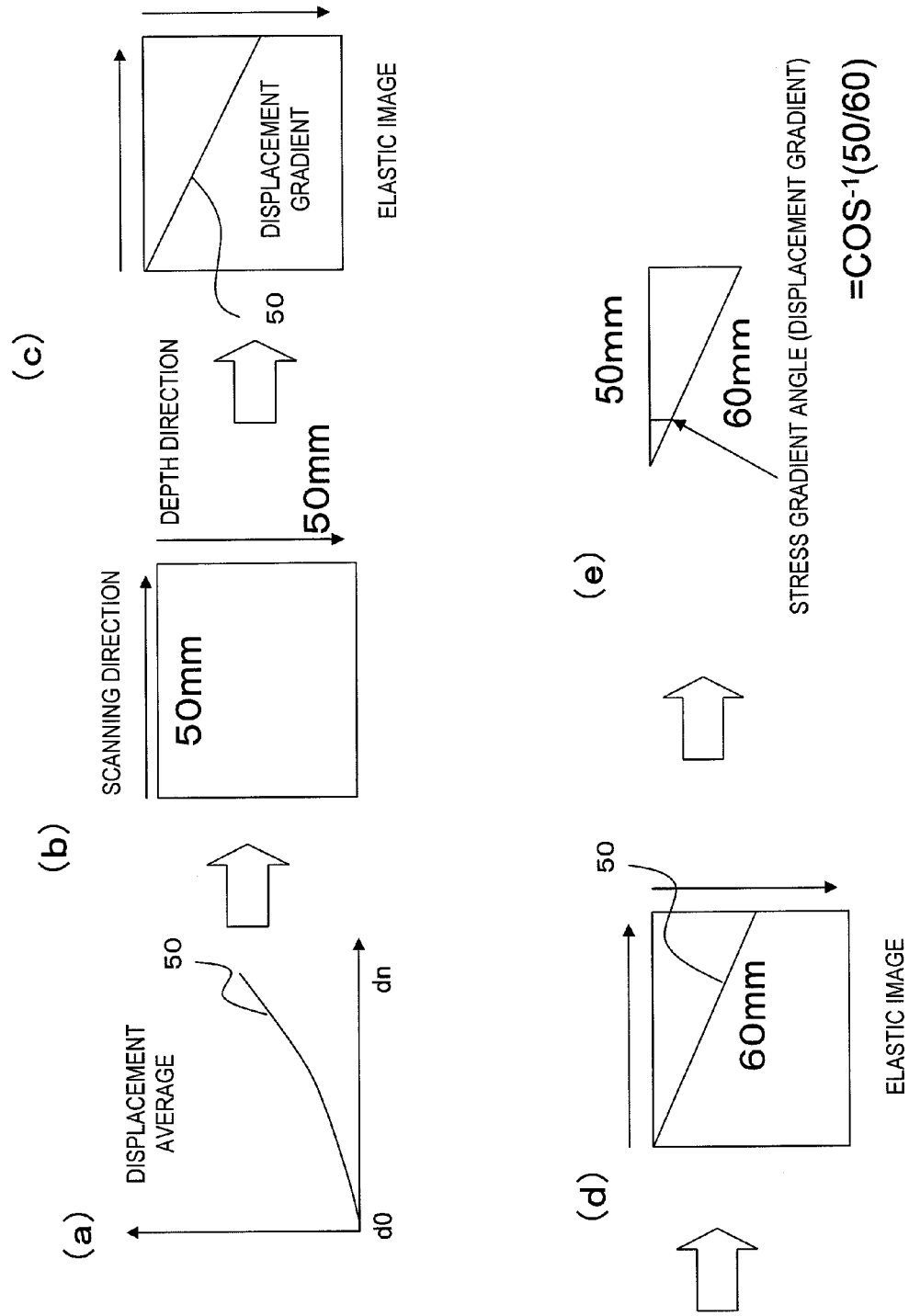
FIG. 15 is a view showing an example of a method of calculating a tilt angle between the pressure direction by pulsation and the ultrasonic wave transmission and reception direction.

FIGS. 14 and 15 are views illustrating processing of the gradient detecting unit 40 and the like in a ninth embodiment. As shown in FIG. 14(a), the gradient detecting unit 40 in this example is configured to include the same displacement gradient calculating circuit 60 as in the first embodiment and a tilt angle calculating circuit 76 which calculates how much the scanning direction of an ultrasonic probe is inclined from the pressure direction by pulsation on the basis of the displacement gradient calculated by the displacement gradient calculating circuit 60. In addition, explanation regarding the same units as in the first embodiment and the like will be omitted.

In this example, when generating an elastic image by pressing tissue in a tomographic portion of the object using pulsation caused by the blood flow, the tilt angle calculating circuit 76 calculates a tilt angle of the scanning direction of the ultrasonic probe with respect to the pressure direction by pulsation on the basis of the displacement gradient, and the ultrasonic wave transmission/reception control unit 17 changes a beam angle of an ultrasonic wave according to the calculated tilt angle.

FIG. 14 is a view showing an example of a method of changing a beam angle of an ultrasonic wave. For example, when acquiring an elastic image of tissue adjacent to the heart or the main artery, such as the liver or the pancreas, tissue distortion may be obtained due to use of the pulsation even if the tissue is not distorted manually or mechanically. However, in order to acquire an elastic image, it is necessary that vectors of the transmission and reception direction of an ultrasonic beam and the distortion direction of tissue are the same or opposite. In other words, it is preferable that the pressure direction by pulsation and the transmission and reception direction of an ultrasonic beam be parallel to each other. However, it may be difficult to dispose the ultrasonic probe 12 in such a preferable state.

Then, as shown in FIG. 14(b), the pressure direction by pulsation and the ultrasonic wave transmission and reception direction obliquely cross each other. In this case, as shown in FIG. 14(c), a gradient occurs in the displacement of tissue along the scanning direction of the ultrasonic probe 12. Then, as shown in FIG. 14(d), the tilt angle calculating circuit 76 calculates how much the scanning direction of the ultrasonic probe 12 is inclined from the pressure direction by pulsation on the basis of the displacement gradient in the scanning direction and transmits the angle correction data corresponding to the calculated tilt angle to the ultrasonic wave transmission/reception control unit 17, and the ultrasonic wave transmission/reception control unit 17 changes the beam angle of an ultrasonic wave so that vectors of the pressure direction by pulsation and the ultrasonic wave transmission and reception direction are the same or opposite.

FIG. 15 is a view showing an example of a method of calculating a tilt angle between the pressure direction by pulsation and the ultrasonic wave transmission and reception direction. First, the displacement gradient calculating circuit 60 calculates a displacement gradient in the same manner as in the first embodiment and the like, as shown in FIG. 15(a). Then, as shown in FIG. 15(b), the tilt angle calculating circuit 76 calculates the image size of a display image in the scanning direction and the depth direction. The display image may be a monochrome B-mode image or an elastic image, for example. Then, as shown in FIG. 15(c), the tilt angle calculating circuit 76 draws the displacement gradient on the elastic image. Then, as shown in FIG. 15(d), the tilt angle calculating circuit 76 calculates the length of the displacement gradient on the display image. Then, as shown in FIG. 15(e), the tilt angle calculating circuit 76 calculates the tilt angle (displacement gradient) in the pressure direction by pulsation and the ultrasonic wave transmission and reception direction by "(displacement gradient)=$COS^{-1}(50/60)$" assuming that the image size in the scanning direction is 50 mm and the length of the displacement gradient is 60 mm, for example.

After the tilt angle is calculated, the tilt angle calculating circuit 76 outputs the angle correction data to the ultrasonic wave transmission/reception control unit 17. The ultrasonic wave transmission/reception control unit 17 changes beam angle of an ultrasonic wave so that vectors of the pressure direction by pulsation and the ultrasonic wave transmission and reception direction are the same or opposite, by controlling the delay time of a transmitted pulse of each beam line according to the angle correction data. According to this example, even if it is difficult that vectors of the pressure direction by pulsation and the ultrasonic wave transmission and reception direction are the same or opposite due to restriction of arrangement of the ultrasonic probe 12, it is possible to make an elastic image using pulsation more suitable for diagnosis.

In addition, the degree of inclination of the ultrasonic probe 12 can be clearly fed back to the examiner by displaying a drawing, which imitates the body surface of the object 10 and the ultrasonic probe 12, on the image display unit 26 and changing the tilt angle of the drawing imitating the ultrasonic probe 12 with respect to the body surface of the object 10 according to the calculated tilt angle of the ultrasonic probe 12 in the scanning direction and displaying it on the image display unit 26.

Embodiment 10

Figure 16:
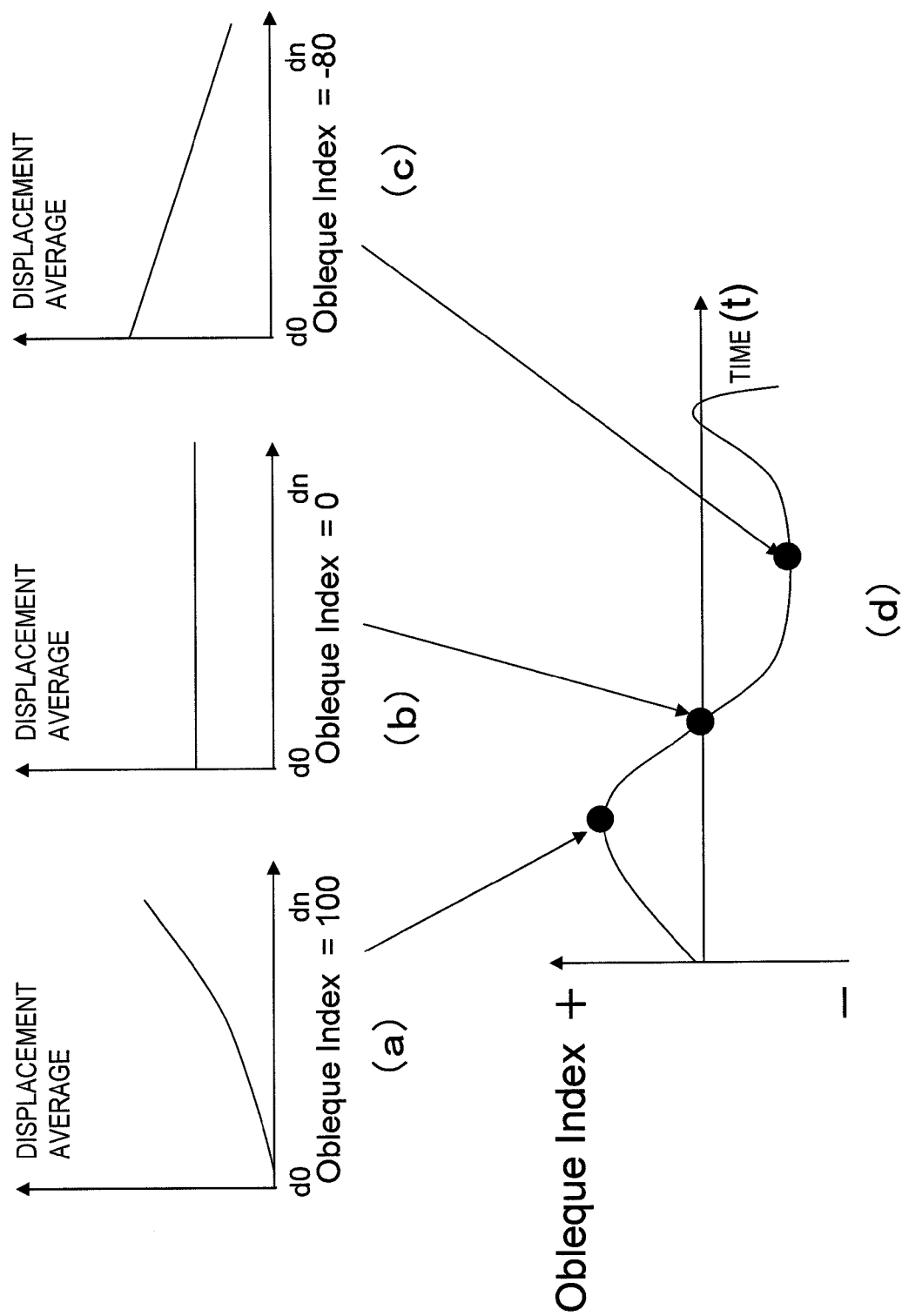
FIG. 16 is a view illustrating processing of a gradient detecting unit and the like in a tenth embodiment.

FIG. 16 is a view illustrating processing of the gradient detecting unit 40 and the like in a tenth embodiment. The detailed configuration of the gradient detecting unit 40 is the same as that in the seventh embodiment. Hereinafter, processing in the tenth embodiment which is executed by the displacement gradient calculating circuit 60, the differential circuit 72, the gradient feature value detecting circuit 74, and the like will be described. In addition, explanation regarding the same units as in the first and seventh embodiments and the like will be omitted. In this example, similarly to the seventh embodiment, the displacement gradient calculating circuit 60 calculates a displacement gradient in a scanning direction for each displacement frame, the differential circuit 72 and the gradient feature value detecting circuit 74 calculate a feature value (Oblique Index) of the displacement gradient on the basis of the calculated displacement gradient, and the displacement gradient feature value is displayed on the image display unit 26 along the time axis using a graph or the like.

When pressing an object manually using the ultrasonic probe 12, the stress in the scanning direction may be uneven due to the influence of the hand shaking of the examiner. This unevenness may change with time like 100 in a certain time phase (a), 0 in a certain time phase (b), and −80 in a certain time phase (c), for example, as shown in FIGS. 16(*a*) to 16(*c*). Therefore, in this example, the displacement gradient calculating circuit 60 calculates a displacement gradient in a scanning direction for each displacement frame, and the differential circuit 72 and the gradient feature value detecting circuit 74 calculate a feature value (Oblique Index) of the displacement gradient on the basis of the calculated displacement gradient. As a result, as shown in FIG. 16(*d*), a change in the displacement gradient feature value with time is graph-displayed with the displacement gradient feature value on the vertical axis and time on the horizontal axis.

According to this example, since a situation of hand shaking can be fed back to the examiner by displaying a temporal change in the displacement gradient feature value (Oblique Index), the quality of pressure can be improved.

Embodiment 11

Figure 17:
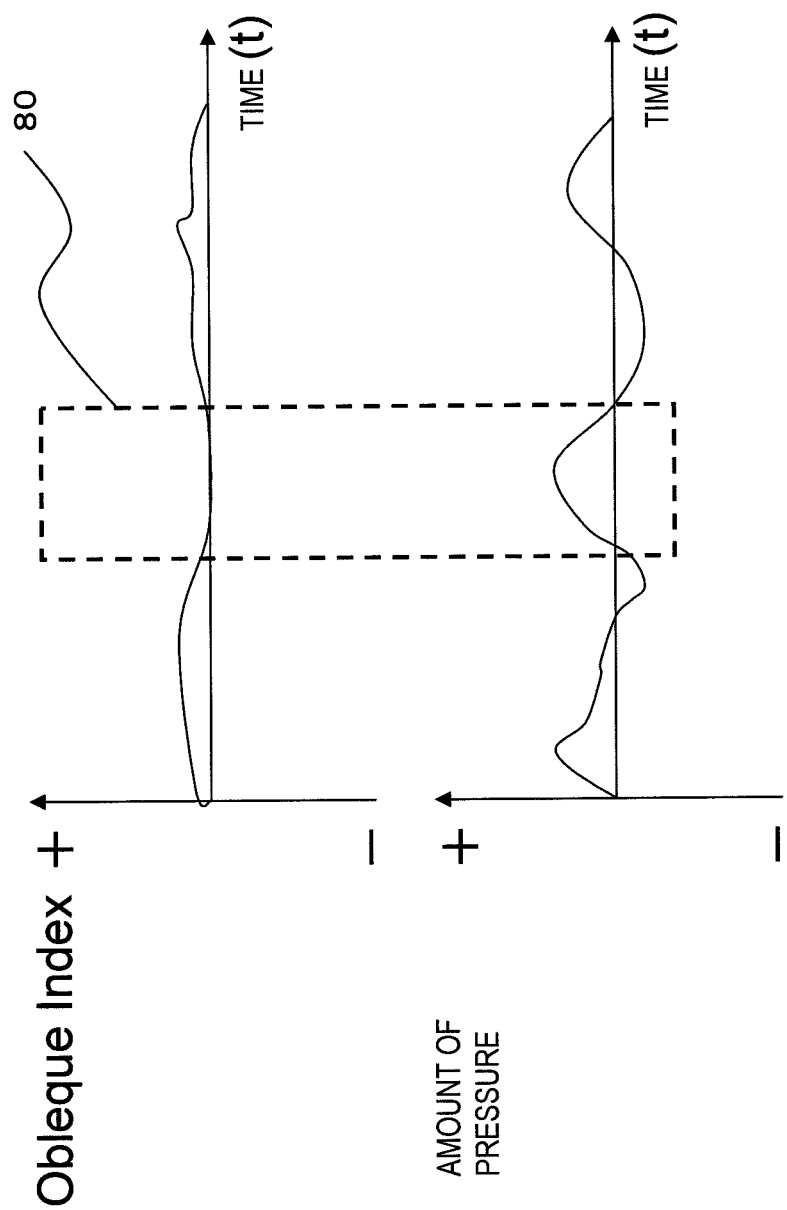
FIG. 17 is a view illustrating processing of a gradient detecting unit and the like in an eleventh embodiment.

FIG. 17 is a view illustrating processing of the gradient detecting unit 40 and the like in a tenth embodiment. The detailed configuration of the gradient detecting unit 40 is the same as that in the seventh embodiment. Hereinafter, processing in the tenth embodiment which is executed by the displacement gradient calculating circuit 60, the differential circuit 72, the gradient feature value detecting circuit 74, and the like will be described. In addition, explanation regarding the same units as in the first and seventh embodiments and the like will be omitted. In this example, a graph of the average value of displacement or the like of tissue in a tomographic portion for each displacement frame along the time axis and a graph of the displacement gradient feature value along the time axis are displayed on the image display unit 26.

Distance measurement or the like using a displacement average, a distortion average, a stress average, and tracking as indices regarding whether or not the pressure of an examiner is appropriate may be mentioned. In this example, however, a temporal change in the displacement gradient feature value (Oblique Index) calculated by the displacement gradient calculating circuit 60, the differential circuit 72, and the gradient feature value detecting circuit 74 in the seventh embodiment and the like and a temporal change in the amount of pressure are simultaneously displayed as an image. As shown in FIG. 17, a temporal change in the displacement gradient feature value (Oblique Index) is displayed in the upper part, and the temporal change in the amount of pressure is displayed in the lower part. The amount of pressure is displacement, elastic information such as distortion or the average of stress, which are calculated by the displacement measuring unit 30, the elastic information calculating unit 32, and the pressure measuring unit 46, respectively. The examiner can acquire an elastic image suitable for diagnosis by improving the quality of pressure by operating the ultrasonic probe 12 so that both the graphs become appropriate.

Moreover, as shown in FIG. 17, it is possible to calculate a time phase in which the gradient feature value is smaller than the threshold value set in advance and the pressure angle of the object by the ultrasonic probe 12 is appropriate and a time phase in which the amount of pressure applied to the object by the ultrasonic probe 12 is appropriate and to display a region where both the time phases overlap as a good image region 80. A plurality of good image regions 80 may also be displayed along the time axis. According to this, since the examiner may operate the ultrasonic probe 12 so that the good image region 80 is continuously displayed, it is possible to acquire an elastic image suitable for diagnosis by performing the pressure technique more appropriately.

A time phase in which the amount of pressure is appropriate can be calculated on the basis of a graph of a temporal change in the amount of pressure. For example, it can be calculated on the basis of the conditions including whether or not the amount of pressure is in a range of the threshold value set in advance and whether or not pressure is smoothly repeated. Whether or not pressure is smoothly repeated may be determined on the basis of the conditions in which the amount of pressure increases in a unit of 0 to ½t and the amount of pressure decreases in a unit ½t to t and bilateral symmetry is obtained accordingly (left-right symmetry) in a unit (for example, 0 to t) until the amount of pressure becomes a negative value after it becomes a positive value, for example. The same is true for a unit until the amount of pressure becomes a positive value after it becomes a negative value.

In addition, it is possible to calculate a time phase in which the displacement gradient feature value is smaller than the threshold value set in advance and the pressure angle of the object by the ultrasonic probe 12 is appropriate and a time phase in which the amount of pressure applied to the object by the ultrasonic probe 12 is appropriate, select a frame in which both the time phases overlap (for example, an elastic image frame) automatically after freezing, and display the elastic image based on the frame on the image display unit 26. According to this, since an elastic image which is suitable for diagnosis due to the good pressure state can be automatically selected, diagnostic efficiency can be improved.

Figure 18:
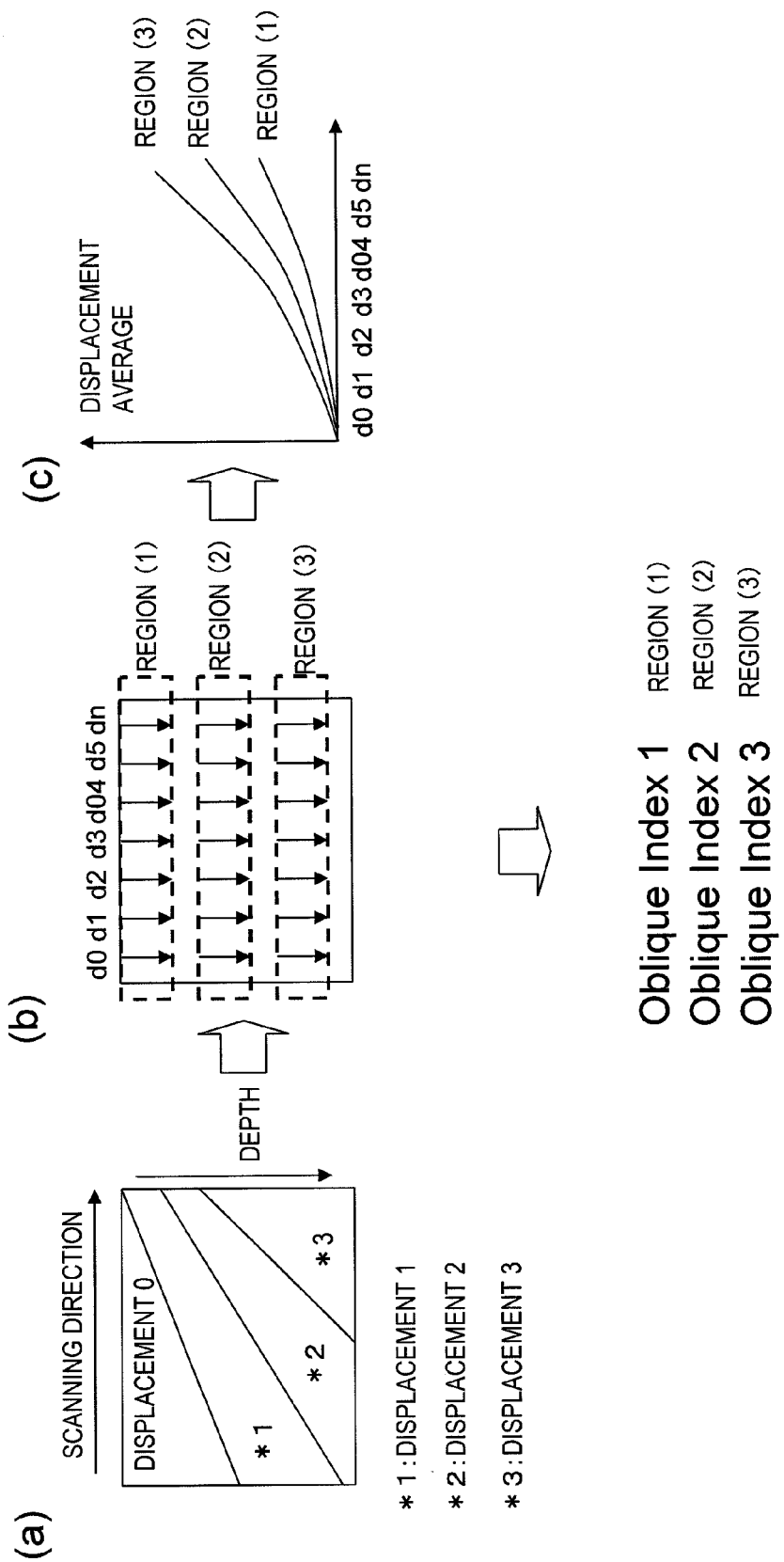
FIG. 18 is a view showing an example of calculating a displacement gradient feature value for each of a plurality of calculation regions (regions of interest) of the displacement gradient feature value set along the depth direction of the beam line of an ultrasonic wave.

In addition, although an example in which the feature value calculation region setting unit 61 sets one feature value calculation region for one frame and the displacement gradient calculating circuit 60, the differential circuit 72, and the gradient feature value detecting circuit 74 calculate one displacement gradient feature value is shown in the above explanation, the feature value calculation region setting unit 61 may set a plurality of feature value calculation regions for one frame and the displacement gradient calculating circuit 60, the differential circuit 72, and the gradient feature value detecting circuit 74 may calculate a plurality of displacement gradient feature values without being limited to this. That is, as shown in FIG. 18, the feature value calculation region setting unit 61 may set a plurality of calculation regions (regions of interest) of the displacement gradient feature value along the depth direction of the beam line of an ultrasonic wave, and the displacement gradient calculating circuit 60, the differential circuit 72, and the gradient feature value detecting circuit 74 may calculate a plurality of displacement feature values for each region by the same operation as in the seventh embodiment and the like.

REFERENCE SIGNS LIST

1: ULTRASONIC DIAGNOSTIC APPARATUS
10: OBJECT
12: ULTRASONIC PROBE
26: IMAGE DISPLAY UNIT
27: RF SIGNAL STORAGE UNIT
28: RF SIGNAL FRAME DATA SELECTING UNIT
30: DISPLACEMENT MEASURING UNIT
32: ELASTIC INFORMATION CALCULATING UNIT
34: ELASTIC IMAGE FORMING UNIT
40: GRADIENT DETECTING UNIT
50: DISPLACEMENT GRADIENT
52: CORRECTION COEFFICIENT
54: CORRECTED DISPLACEMENT GRADIENT
56: STRESS DISTRIBUTION COEFFICIENT

The invention claimed is:

1. An ultrasonic diagnostic apparatus comprising:
an ultrasonic probe which transmits and receives an ultrasonic wave to and from an object;
a displacement measuring unit configured to measured displacement on the basis of a reflected echo signal measured by the ultrasonic probe;
an elastic image forming unit configured to form an elastic image on the basic of the measured displacement;
an image display unit configured to display the elastic image; and
a gradient detecting unit configured to calculate a displacement gradient of said ultrasonic probe in a scanning direction perpendicular to an ultrasonic wave transmission and reception direction and calculating a correction coefficient on the basis of the calculated displacement gradient,
wherein the elastic image forming unit corrects the elastic image on the basis of the calculated correction coefficient,
wherein the gradient detecting unit calculates a displacement gradient feature value on the basis of the displacement gradient in the scanning direction for each frame of displacement of tissue in a tomographic portion based on a pair of RF signal frame data items acquired at different times,
wherein the ultrasonic diagnostic apparatus further comprising:
as image mixing unit configured to generate the elastic image by selecting a plurality of displacement frames, each of which has the smaller displacement gradient feature value than a threshold value set in advance, and
wherein a plurality of elastic information frames based on the plurality of displacement frames, or a plurality of elastic image frames based on the plurality of displacement frames and mixing the plurality of selected frames is included.

2. The ultrasonic diagnostic apparatus according to claim 1,
wherein the image mixing unit selects a plurality of displacement frames each of which has the smaller displacement gradient feature value than the threshold value set in advance, corrects each of the plurality of selected displacement frames on the basis of a correction coefficient with respect to the displacement of each beam line, selects the plurality of corrected displacement frames, a plurality of elastic information frames based on the plurality of corrected displacement frames, or a plurality of elastic image frames based on the plurality of corrected displacement frames, and mixes the plurality of selected frames to generate the elastic image.

3. An ultrasonic diagnostic apparatus comprising:
an ultrasonic probe which transmits and receives an ultrasonic wave to and from an object;
a displacement measuring unit configured to measured displacement on the basis of a reflected echo signal measured by the ultrasonic probe;
an elastic image forming unit configured to form an elastic image on the basic of the measured displacement;
an image display unit configured to display the elastic image; and
a gradient detecting unit configured to calculate a displacement gradient of said ultrasonic probe in a scanning direction perpendicular to an ultrasonic wave transmission and reception direction and calculating a correction coefficient on the basis of the calculated displacement gradient,
wherein the elastic image forming unit corrects the elastic image on the basis of the calculated correction coefficient, and
wherein when generating the elastic image by pressing tissue in a tomographic portion of the object using pulsation caused by the blood flow, the gradient detecting unit calculates a tilt angle of the scanning direction of the ultrasonic probe with respect to a pressure direction by the pulsation on the basis of the displacement gradient in the scanning direction and changes a beam angle of the ultrasonic wave according to the calculated tilt angle.

4. An ultrasonic diagnostic apparatus comprising:
an ultrasonic probe which transmits and receives an ultrasonic wave to and from an object;
a displacement measuring unit configured to measured displacement on the basis of a reflected echo signal measured by the ultrasonic probe;
an elastic image forming unit configured to form an elastic image on the basic of the measured displacement;
an image display unit configured to display the elastic image; and
a gradient detecting unit configured to calculate a displacement gradient of said ultrasonic probe in a scanning direction perpendicular to an ultrasonic wave transmission and reception direction and calculating a correction coefficient on the basis of the calculated displacement gradient, wherein the elastic image forming unit corrects the elastic image on the basis of the calculated correction coefficient, wherein the gradient detecting unit calculates a displacement gradient feature value on the basis of the displacement gradient in the scanning direction for each displacement frame of tissue in the tomographic portion based on a pair of RF signal frame data items acquired at different times, and wherein the calculated displacement gradient feature value is graph-displayed on the image display unit along a time axis.

5. The ultrasonic diagnostic apparatus according to claim 4, wherein a graph of an average value of displacement of the tissue in the tomographic portion for each displacement frame along the time axis and a graph of the displacement gradient feature value along the time axis are displayed on the image display unit, and wherein a time phase in which the amount of pressure applied to the object by the ultrasonic probe is appropriate and a time phase in which the displacement gradient feature value is smaller than a threshold value set in advance and a pressure angle of the object by the ultrasonic probe is appropriate are calculated on the basis of the graph of the average value of displacement of the tissue in the tomographic portion along the time axis, and an elastic image in a time phase in which both the amount of pressure and the pressure angle are appropriate is selected and displayed on the image display unit.

6. An ultrasonic diagnostic apparatus comprising:

an ultrasonic probe which transmits and receives an ultrasonic wave to and from an object;

a displacement measuring unit configured to measured displacement on the basis of a reflected echo signal measured by the ultrasonic probe;

an elastic image forming unit configured to form an elastic image on the basic of the measured displacement;

an image display unit configured to display the elastic image; and a gradient detecting unit configured to calculate a displacement gradient of said ultrasonic probe in a scanning direction perpendicular to an ultrasonic wave transmission and reception direction and calculating a correction coefficient on the basis of the calculated displacement gradient, wherein the elastic image forming unit corrects the elastic image on the basis of the calculated correction coefficient, wherein the gradient detecting unit calculates a tilt angle of the ultrasonic probe in the scanning direction on the basis of the displacement gradient in the scanning direction, and wherein a tilt angle of a drawing imitating the ultrasonic probe with respect to the body surface of the object on a drawing imitating the body surface of the object and the ultrasonic probe is changed according to the tilt angle of the ultrasonic probe in the scanning direction and the changed tilt angle is displayed on the image display unit.

* * * * *